US010218411B2

(12) United States Patent
Rovatti

(10) Patent No.: US 10,218,411 B2
(45) Date of Patent: Feb. 26, 2019

(54) METHOD FOR PROVIDING OPERATION DATA TO A FLUID PROCESSING MEDICAL APPARATUS USING A MEDICAL ACCESSORY

(71) Applicant: GAMBRO LUNDIA AB, Lund (SE)

(72) Inventor: Paolo Rovatti, Modena (IT)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 15/519,013

(22) PCT Filed: Oct. 15, 2015

(86) PCT No.: PCT/EP2015/073944
§ 371 (c)(1),
(2) Date: Apr. 13, 2017

(87) PCT Pub. No.: WO2016/059184
PCT Pub. Date: Apr. 21, 2016

(65) Prior Publication Data
US 2017/0237467 A1  Aug. 17, 2017

(30) Foreign Application Priority Data

Oct. 17, 2014  (EP) .................................... 14189408

(51) Int. Cl.
H04B 7/00      (2006.01)
H04B 5/00      (2006.01)
(Continued)

(52) U.S. Cl.
CPC ............ H04B 5/0031 (2013.01); A61M 1/14 (2013.01); G06F 3/041 (2013.01); G06F 19/00 (2013.01);
(Continued)

(58) Field of Classification Search
CPC ....... H04B 5/0031; G06F 12/00; H04W 4/008
(Continued)

(56) References Cited

U.S. PATENT DOCUMENTS

2005/0064814 A1* 3/2005 Matsuo .............. G06K 7/10237
455/41.1
2006/0242293 A1* 10/2006 Russ ........................ A61B 5/00
709/224
(Continued)

FOREIGN PATENT DOCUMENTS

EP      2706726       3/2015
WO   WO 2008/129344   10/2008

OTHER PUBLICATIONS

PCT International Search Report and Written Opinion for PCT/EP2015/073944 dated Jan. 12, 2016 (14 pages).
(Continued)

Primary Examiner — Md K Talukder
(74) Attorney, Agent, or Firm — Mueting, Raasch & Gebhardt, P.A.

(57) ABSTRACT

A method for providing operation data to a fluid processing medical apparatus and a medical accessory have been provided. The method comprises the steps of providing the medical apparatus (10) with a readable element (12); acquiring configuration data associated to the readable element (12) of the medical apparatus (10) by relatively approaching a data acquisition unit (22) of a medical accessory (20) and the readable element (12) of the medical apparatus (10); establishing a wireless communication between medical accessory (20) and the medical apparatus (10) based on the configuration data; providing a medical component (40) having a readable element (42); acquiring operation data associated to the readable element (42) of the medical component (40) by relatively approaching the data acquisition unit (22) of the medical accessory (20) and the readable
(Continued)

element (42) of the medical component (40), the medical component (40) being destined to be operatively coupled to the medical apparatus (10); and providing the operation data to the medical apparatus (10) using the wireless communication.

23 Claims, 5 Drawing Sheets

(51) Int. Cl.
| | | |
|---|---|---|
| *H04W 4/80* | (2018.01) | |
| *A61M 1/14* | (2006.01) | |
| *G06F 19/00* | (2018.01) | |
| *H04W 4/02* | (2018.01) | |
| *H04W 12/02* | (2009.01) | |
| *G16H 40/63* | (2018.01) | |
| *H04W 76/38* | (2018.01) | |
| *G06F 3/041* | (2006.01) | |
| *G06K 7/10* | (2006.01) | |
| *G06K 19/06* | (2006.01) | |
| *H04M 1/02* | (2006.01) | |

(52) U.S. Cl.
CPC ....... *G06F 19/3468* (2013.01); *G06K 7/1092* (2013.01); *G06K 19/06112* (2013.01); *G16H 40/63* (2018.01); *H04B 5/0037* (2013.01); *H04W 4/02* (2013.01); *H04W 4/023* (2013.01); *H04W 4/80* (2018.02); *H04W 12/02* (2013.01); *H04W 76/38* (2018.02); *A61M 2205/12* (2013.01); *A61M 2205/3561* (2013.01); *A61M 2205/3569* (2013.01); *A61M 2205/505* (2013.01); *A61M 2205/6018* (2013.01); *A61M 2205/6072* (2013.01); *A61M 2230/30* (2013.01); *H04M 1/0202* (2013.01)

(58) Field of Classification Search
USPC ...................................... 455/41.1, 41.2, 41.3
See application file for complete search history.

(56) References Cited

U.S. PATENT DOCUMENTS

| | | | | |
|---|---|---|---|---|
| 2007/0229018 A1* | 10/2007 | Mitchell | .............. | G01R 31/343 318/650 |
| 2007/0255116 A1* | 11/2007 | Mehta | ................. | A61B 5/0002 600/300 |
| 2010/0282834 A1* | 11/2010 | Devergne | ................ | A61M 1/16 235/375 |
| 2011/0028094 A1* | 2/2011 | Masuda | ................ | H04L 63/107 455/41.2 |
| 2012/0330769 A1* | 12/2012 | Arceo | .................... | G06Q 20/32 705/21 |
| 2014/0061306 A1* | 3/2014 | Wu | ..................... | G06K 7/10386 235/439 |
| 2014/0148104 A1* | 5/2014 | Marterstock | ............ | A61M 1/14 455/73 |
| 2014/0236819 A1* | 8/2014 | Pillay | ................... | G06Q 20/108 705/42 |
| 2015/0237838 A1* | 8/2015 | Hay | ................... | A01K 67/0339 800/13 |
| 2016/0261974 A1* | 9/2016 | Arrizza | ............... | A61M 1/1603 |
| 2016/0330573 A1* | 11/2016 | Masoud | ................. | H04W 4/90 |
| 2016/0361492 A1* | 12/2016 | Nunez | .............. | A61M 16/0003 |
| 2017/0172415 A1* | 6/2017 | Wik | ........................ | H04W 4/80 |
| 2017/0239412 A1* | 8/2017 | Court | ..................... | H04L 67/12 |

OTHER PUBLICATIONS

European Extended Search Report for Application No. 14189408.9-1951 dated May 7, 2015 (8 pages).
Anonymous "Bar Code Handy Scanner—Denso Wave—Wireless Models", XP-00273 8544, Jul. 18, 2014.
Steinfeld, et al., "Is Embedded Going Net-Crazy?—A Response", Internet Citation, Mar. 29, 2001, XP002348224, retrieved from the internet: URL:http://www.developonline.com/community/ed_resource/feature_article/13699?print [retrieved on Oct. 5, 2006].
Mossman, John, "Important Considerations for Infusion Pump and Portable Medical Designs", Internet Archive (archivation dated Jun. 28, 2014) May 10, 2010, retrieved from the internet: URL:http://web.archive.org/web/20140628171444/https://www.maximintegrated.com/en/app-notes/index.myp/id/4677 [retrieved on Jul. 17, 2018].
Anonymous: "GT10B-SB GT10B-LB User's Manual", Denso, Sep. 1, 2008, retrieved from the internet URL:http://www.anthinh.com/files, download/728 [retrieved on Jul. 19, 2018].
PCT International Search Report and Written Opinion for PCT/EP2015/074038 dated Dec. 16, 2015 (14 pages).
European Extended Search Report for Application No. 14189409.7-1853 dated Apr. 2, 2015 (9 pages).

* cited by examiner

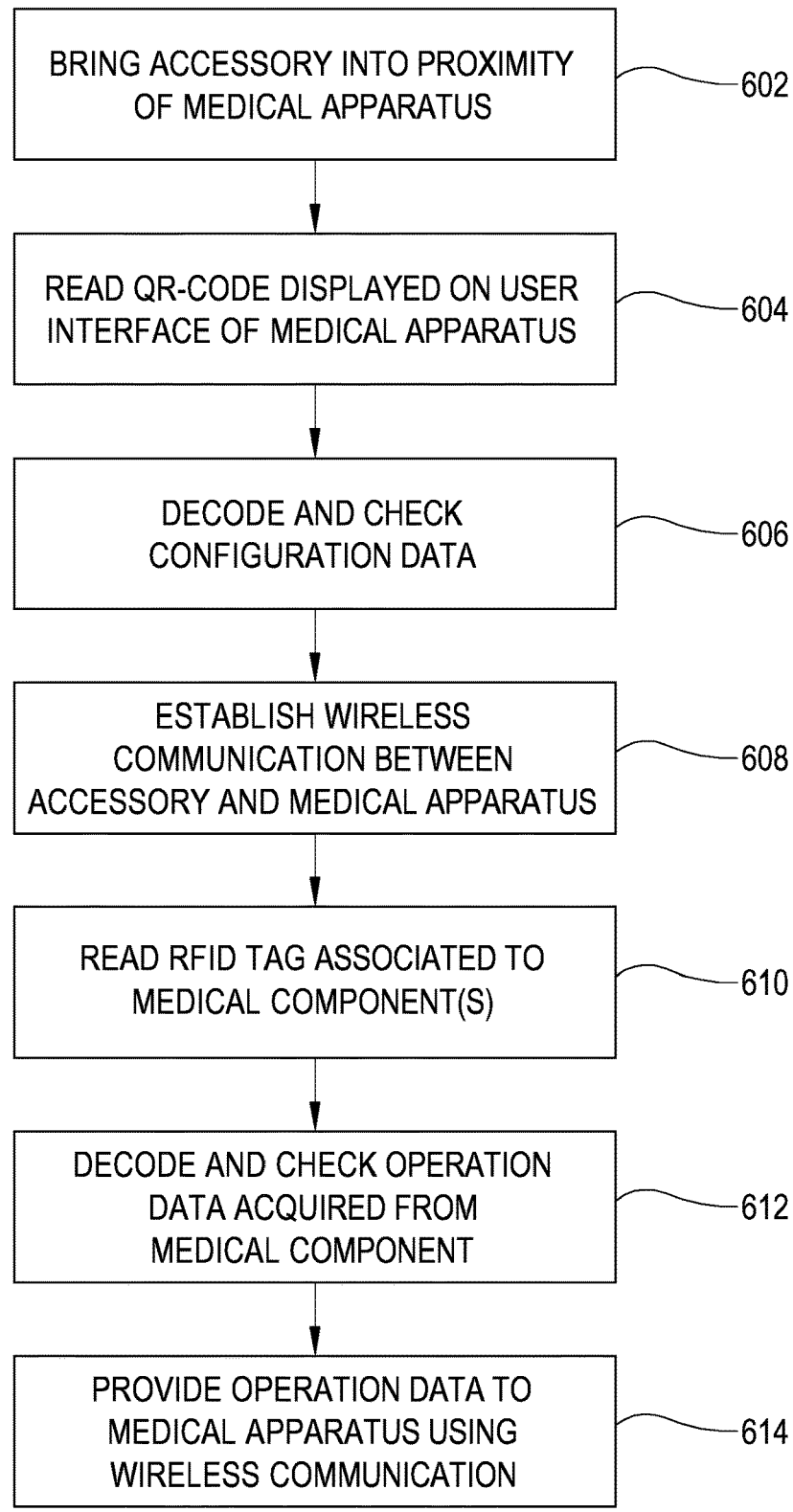

METHOD FOR PROVIDING OPERATION DATA TO A FLUID PROCESSING MEDICAL APPARATUS USING A MEDICAL ACCESSORY

This is a U.S. National Stage Application of International Application No. PCT/EP2015/073944, filed Oct. 15, 2015, which was published in English on Apr. 21, 2016 as International Publication No. WO 2016/059184 A1. International Application No. PCT/EP2015/073944 claims priority to European Application No. 14189408. filed Oct. 17, 2014.

DESCRIPTION

The present invention relates to a method for providing operation data to a fluid processing medical apparatus, such as a blood treatment apparatus, using a data acquisition unit. The operation data generally pertain to one or more—generally disposable or replaceable—medical components, configured to be operably coupled to the fluid processing medical apparatus/blood treatment apparatus. The present invention further relates to a data acquisition unit, and a fluid processing medical system comprising the data acquisition unit, employing the aforementioned method, the system being configured for receiving one or more medical components. The present invention further relates to a system comprising a plurality of fluid processing medical apparatus and data acquisition units between which operation data is being provided. Within the scope of the present description, a fluid processing medical apparatus includes an infusion pump and a blood treatment apparatus, i.e. a medical device configured for treatment of a patient's blood, for example, a medical device comprising a hemofilter, a plasmafilter, a dialyzer, a hemodiafilter, an ultrafilter, and/or other.

In the following description reference is made specifically to a blood treatment apparatus, particularly an extracorporeal blood treatment apparatus; however it is within the scope of the invention a method for providing operation data to a fluid processing medical device in general and to an infusion pump in particular, too.

In other terms, unless specified the method steps and the technical features referred to the blood treatment apparatus should be considered to be referred to a fluid processing treatment apparatus being for example an infusion pump, too.

The method facilitates providing operation data to a blood treatment apparatus by providing the blood treatment apparatus with a readable element, for example an optically (e.g. bar code or QR code) or electromagnetically (e.g. using a near field communication (NFC) unit such as a radio-frequency identification (RFID) tag) readable code, and to acquire configuration data using a data acquisition unit (e.g. an optical or electromagnetic reader) for establishing a wireless communication between the data acquisition unit and the blood treatment apparatus. The data acquisition unit is then operably linked to the blood treatment apparatus using the wireless communication and may be used to read operation data from medical components and to provide the operation data read by the data acquisition unit to the blood treatment apparatus. For example using an optical reader, the data acquisition may scan a QR code displayed on a blood treatment apparatus and subsequently establish a secure and verified wireless communication based on the configuration data encoded in the QR code. The blood treatment apparatus may provide a QR code containing, for example, configuration data in the form of a unique identification datum or one or more communication parameters (e.g. network address, encryption data, other authentication or identification data, etc.) which enable the data acquisition unit to positively identify the blood treatment apparatus and to establish the wireless communication with the identified apparatus.

Acquiring the configuration data requires the data acquisition unit to be in proximity to the blood treatment apparatus, due to a configured maximum operating distance of the optical and/or electromagnetic reader. In detail, a reading portion of the data acquisition unit is required to be put into proximity to the readable element comprised in the blood treatment apparatus, since it is these entities (i.e. units and elements) between which the configuration data necessary for establishing the wireless communication is transferred. It is, however, understood that the proximity of the reading portion and the readable element typically requires the unit and the device also being in proximity to each other.

The wireless communication established between the data acquisition unit and the blood treatment apparatus facilitates providing the blood treatment apparatus with operation data. Such data may be acquired in the same manner as the configuration data that is necessary for operably linking the data acquisition unit and the blood treatment apparatus based on the wireless communication. For example, operating the blood treatment apparatus may require one or more—possibly disposable or replaceable—medical components to be operably coupled to the blood treatment apparatus. Such medical components include, for example, filters, concentrate cartridges, containers providing fresh fluid or receiving waste fluids, fluid lines and fluid line sets, etc. If a filter is to be operably coupled to the blood treatment apparatus, an optical reader of the data acquisition unit may scan, for example, a QR code attached to the filter and provide the operation data decoded from the QR code to the blood treatment apparatus prior to coupling the filter to the apparatus. The blood treatment apparatus may then check the operation data received, for example, against a list of filter types cleared for operation with the apparatus and/or a treatment to be performed and/or an expiration date. In case the filter matches the type required (and, possibly, in case one or more other requirements are met on the side of the apparatus and/or the medical component or components), the blood treatment apparatus may provide an output signal, for example to medical personnel setting up the apparatus, indicating that the filter may be operably coupled to the apparatus at a respective operating area configured for receiving the filter.

In this manner, a user may operably couple the one or more medical components required for a particular treatment session to the blood treatment apparatus and check at the same time whether the medical components comply with the requirements of the apparatus and/or the treatment session. This may facilitate a safe, efficient, and easy setup of the blood treatment apparatus. This may also ensure safe and reliable operation of the blood treatment apparatus.

Further, the data acquisition unit need not be permanently linked to (or fixedly installed in, or be part of) a particular blood treatment apparatus. As the communication link between a data acquisition unit and a particular blood treatment apparatus may be established and closed as required, and since the data acquisition unit might only be required in certain phases (e.g. a setup-phase of the blood treatment apparatus) of the treatment, a single data acquisition unit, or a comparably small number thereof, may be used in combination with a comparably larger number of blood treatment apparatus (e.g. for regularly setting up these apparatus). In a clinical setting, a small number (e.g., 1-5) of data acquisition units (e.g. optical code readers) may be used together with a large number (e.g. 20 or 30) of blood treatment apparatus. Such a 1:n relationship of data acquisition units to blood treatment apparatus may reduce costs for equipment and reduce maintenance requirements.

The invention may further provide an efficient mechanism for establishing a wireless operating communication without necessitating extensive input of configuration or other data and/or corresponding I/O components (e.g. display, touch panel, keyboard, and/or other).

In some cases, different kinds of readable elements may be provided in order to improve efficiency, safety, and/or flexibility. For example, an optical pattern necessary for acquiring the configuration data may be display, whenever required, on a display unit (e.g. touch screen) associated to the blood treatment apparatus. This—in comparison to a (fixed) printed pattern—may facilitate encoding transient configuration data in an optical code, thereby providing, for example, up to date status information about the blood treatment apparatus, or regularly changed encryption data in order to ensure safe operation of the apparatus.

BACKGROUND

Generally, wireless data communication between different devices is known and used in different fields of technology. In many fields of technology, it is desirable to replace or avoid wired data communication in order to alleviate the drawbacks usually associated with wired data communication.

Such drawbacks include, for example, that the physical cables or leads required for corresponding connections may pose a safety hazard in that they may interfere with human users operating the connected components. In particular, if many cable connections are present, managing the cables and ensuring that the connections are not inadvertently interrupted may become a cumbersome task. In addition to electric wiring, medical machines such as blood treatment machines may exhibit a number of other similar connections, for example, blood lines and/or medical fluid lines. Consequently, if many connections are present, a disconnection or erroneous connection may pose a more or less critical risk for the treatment and/or the patient.

In some environments, electromagnetic or other interference may negatively affect the wired connections. Additionally, connections between different devices and/or from a device to a wall outlet may restrict the placement of the devices with respect to one another and/or with respect to the outlet or outlets. Consequently, the electrical layout of the environment in which the devices are to be operated has to be configured for operation of the machines. However, often the electrical layout would have to be adapted as the devices change over time and/or if the environment changes (e.g., if the devices have to be moved from one room to another). In most cases, the electrical layout cannot easily be adapted, because of the necessary construction work associated with changes to the internal wiring of a room or building.

Moving devices around might require connections being interrupted and subsequently re-established in that cables need to be unplugged and plugged in again. Common networking connections might additionally require corresponding patching of connections at a central location (i.e. physically disconnecting and re-connecting of patch cables at, for example, a patch panel and/or a network switch).

In case of medical accessories that are designed to, for example, acquire physical data (e.g. pressure, heart rate, temperature, etc.) from a patient before, during, or after treatment, the use of a medical accessory that relies on a wired connection to other components very much restricts the mobility of the patient.

In some cases, while the patient might be restricted in some manner depending upon treatment or medical condition, the use of medical accessories attached to or otherwise carried by the patient might not require any particular restriction. For example, the medical accessory might facilitate monitoring of patient parameters over a longer period of time, in which the patient is generally present within the hospital, without requiring being connected to any particular machine or outlet.

In case of medical accessories, for example those designed to be operated by medical personnel, cost consideration are generally to be taken into account. While it might be convenient to provide each apparatus with a corresponding accessory it might be uneconomical or even prohibitively costly to do so. For example, some accessories might only be required for a fraction of the entire treatment time. However, if such accessories are fixedly integrated of otherwise permanently connected to a single apparatus, it is not possible to use these accessories with another apparatus, even if the accessories are not is use for certain periods of time.

In case of setting up a blood treatment apparatus for a treatment session, a medical accessory for acquiring operation data from medical components that are to be operably coupled to the blood treatment apparatus is typically required solely during the setup phase of the blood treatment apparatus (e.g. several minutes), but not during the entire treatment time (e.g. several hours). In such a setup phase, medical personnel typically use a data acquisition unit (e.g. an optical reader) in order to scan optical codes provided on replaceable medical components (e.g. blood sets, filters, containers, cartridges, etc.) before the medical components are operably coupled to the blood treatment apparatus. The optical codes may contain, for example, operation data that, once provided by the data acquisition unit to the blood treatment apparatus, may be checked for compliance with the type of apparatus or a treatment session to be performed. Similarly, the optical codes may contain data indicative of a medical agent contained in a concentrate cartridge or container, physical properties of a blood set, and/or operating properties of a filter. Generally, the blood treatment apparatus is provided by the data acquisition unit with the relevant data on medical components to be operably coupled thereto, thereby facilitating checking the data for compliance and signaling any issues, e.g. to medical personnel, before allowing coupling of the medical components to the apparatus. If all data meet the requirements, the medical components may be operably coupled to the apparatus and the treatment may be initiated.

If the data acquisition unit is fixedly installed in the blood treatment apparatus, the unit typically cannot be used during the entire treatment session, but only after the treatment is finished and the apparatus is set up for another treatment session. From an economical point of view, idle time of resources may be regarded as incurring avoidable costs.

Wireless communication may be used in order to provide the data acquisition unit and the blood treatment apparatus with a temporary connection, which may be closed upon completion of the setup phase of the apparatus. The medical personnel may then take the data acquisition unit, typically a compact and/or mobile device (e.g. a bar code scanner or a smart phone equipped with a camera and/or with an NFC data equipment), and use it to set up another blood treatment apparatus. In this manner, a single data acquisition unit (or a comparably small number of the same) may be used in regularly setting up a large number of blood treatment apparatus. In a clinical setting, for example, a single data acquisition unit may be assigned to a group of blood treatment apparatus and/or to an entire ward, team, or unit.

Wireless data connections may alleviate or avoid one or more of the above drawbacks of wired connections, but may entail other drawbacks.

One significant drawback of wireless connections is that wireless connections are typically more difficult to set up than wired connections. In the case of the latter, a user may simply use a suitable cable, identify the two devices to be connected (or one device and a wall outlet), and plug in the connectors located on each end of the cable. Typically, the connectors are configured to connect only to a matching socket in a single manner (e.g. orientation, male/female plugs, color coding, etc.), thereby ensuring a proper connection. In particular, there is very little chance for two devices being connected unintentionally, due to the devices having to be present and the user having to physically identify and connect the devices on-site.

Wireless connections cannot be established in the same way as wired connections, due to the lack of a tangible connection medium. In contrast, the transceiver units integrated into wireless devices have to be programmed and configured to connect with corresponding counterparts, wherein all devices that are intended to participate in wireless data communication with each other have to operate in accordance with the same communication protocols and standards and have to be configured in a manner corresponding to each other (e.g. requiring matching configuration data).

For example, the Wireless Local Area Network (WLAN) IEEE 802.11 standards include media access control (MAC) and physical layer (PHY) specifications for implementing wireless local area network (WLAN) computer communication in the 2.4, 3.6, 5 and 60 GHz frequency bands. In order for a device to establish a data communication using WLAN, corresponding hard- and software components are necessary, as well as a configuration that typically has to be provided upon on-site integration of the device into a WLAN network and/or WLAN ad-hoc connection.

This configuration may include, for example, several technical parameters depending upon the local network configuration. In some examples, a user wishing to integrate a device into a WLAN has to provide the correct Service Set Identifier (SSID) or "network name" the local network has been given, the correct channel (corresponding to a particular frequency or frequency range) that the local network operates on, and—if used—the correct encryption parameters (e.g. a pre-shared key or other credentials) that are required by the encryption standard used (e.g. wired protected access (WPA, WPA2), wired equivalent privacy (WEP), etc.).

Depending upon additional network protocols, the user might have to specify additional networking parameters. For example, if the transmission control protocol/internet protocol (TCP/IP) is used as the transport and network layer, then it might be necessary for the user to provide IP addresses for the device itself, a gateway, a router, one or more name servers (for the domain name system (DNS)), one or more proxies, and/or other devices, as well as further technical parameters (e.g. a subnet mask, etc.).

WO 2008/129344 (A1) describes a method for setting up a fluid treatment apparatus using a single and always accessible reader of information relating to replaceable components, which are to be mounted on the apparatus to perform the fluid treatment. A fluid treatment apparatus having a reader that is always accessible is also described. The reader may also be relied on to enter information other that those relating to the replaceable components, such as commands for the apparatus, patient related information, etc.

One significant factor is that the setting up of a wireless operating communication is a non-trivial task requiring some expertise in the field of wireless communications. Often, medical personnel operating the devices and accessories are not trained to be sufficiently proficient in setting up and running extensive networks of many devices and accessories that are linked in a wireless network. Further, even if the medical personnel were sufficiently proficient, or even if a supporting staff of technicians were available to fulfill such duties, the problem of securing safe operation of the multiple devices and accessories remains.

In day to day operations, typically many accessories need to be linked wirelessly to a number of devices, wherein a medical accessory may be, for example, associated to a first patient and linked to a first device (e.g. a blood treatment apparatus) in the morning. Subsequently, the patient has to undergo a different treatment and the wireless operating communication between the medical accessory and the first device is closed and a wireless operating communication to a second device has to be established later in the morning. In the afternoon, the medical accessory may be associated to a second patient undergoing the same or another series of treatments, again requiring several times establishing and closing communication with one or more devices.

In the above-mentioned example of a data acquisition unit being temporarily put into wireless communication with a blood treatment apparatus, the data acquisition unit may be used to set up a large number of blood treatment apparatus, all the while establishing and closing wireless communication with each apparatus for the time required to set up the apparatus.

All this time it must be ensured that the wireless operating communication is established between the devices and accessories that are actually intended to be linked together. In some cases, a number of blood treatment apparatus may be located in a single room and a number of patients undergoing blood treatment and each provided with their individual medical accessory (e.g. a pressure cuff) need to be taken care of, requiring being connected to a respective blood treatment apparatus and also requiring the medical accessory being put into wireless operating communication with the respective blood treatment apparatus. It is apparent that a misconfiguration of the wireless operating configuration (e.g., leading to the medical accessory of one patient being mistakenly put into wireless operating communication not with the corresponding blood treatment apparatus, but another one next to the correct one) may lead to potentially disastrous effects for the health of either patient being treated in connection with any of the affected apparatus and/or accessories. Therefore, it is imperative that a wireless operating communication is established only between the apparatus and accessories for which the communication is intended.

The above particularly applies to wireless communication between a data acquisition unit and a blood treatment apparatus, due to the importance of correctly setting up the apparatus. Also, if the data acquisition unit is required to open and close wireless communication with a large number of apparatus in a short time, an efficient, safe, easy to use, and reliable manner of doing so is necessary. Ideally, the data acquisition unit may accommodate multiple different technical means with which to acquire data (e.g. by optical scanner or camera, or by electromagnetic data transfer using RFID or similar). Further, the data acquisition unit may employ the same technical means in order to acquire configuration data necessary for establishing a wireless communication with a blood treatment apparatus and in order to acquire operation data from the medical components to be provided to the blood treatment apparatus. It is understood that the data acquisition unit may support multiple different technical means for data acquisition and communication at the same time, any one of which may be employed, also in a mixed mode (e.g. using RFID in order to acquire configuration data and using an optical QR code scanner or a camera in order to acquire operating data) depending upon the technical properties of the blood treatment apparatus and/or the (replaceable) medical components.

It is further obvious that the above-described effects and problems affect any device and any accessory potentially connected to a same network or to each other—regardless of the location or type of the device or accessory. Due to the wireless communication and, possibly, a common network providing a supporting infrastructure, a medical accessory may potentially establish a wireless operating communication with any suitable device on the network (e.g. irrespective of the location of the device), such that operation data, patient data, treatment data, or any other data may be transmitted on a regular basis and independently from the location of either device/accessory. For example, a physician may collect the history of the blood pressure and other patient parameters over a period of time where the patient is present within a hospital. During this time, the accessory associated with the patient and wirelessly linked to the device used by the physician for his monitoring of the patient's data, may transmit the patient data on a regular basis before, during, and after a treatment session. At the same time, the accessory may be configured to establish a wireless operating communication (also) with a blood treatment apparatus for the period it takes for the patient to undergo a blood treatment session, thereby providing patient data (also) to the blood treatment machine. All this requires that the accessory may be safely configured to establish and close wireless operating connections with different devices.

Another significant factor in setting up wireless devices is that typically the input of the aforementioned configuration data requires corresponding input and output components, for example a display, keyboard, etc. While some devices already necessitate such I/O components for their intended use (e.g. personal computers, tablet computers, etc.), therefore being equipped with these components in any case, some other devices may be operated without the need for any such I/O components designed for user interaction, therefore lacking such I/O components. Some medical accessories may be designed to merely be in data communication with another device in order to take measurements and to transmit the measured value or values taken to the other device without providing a display or a keyboard. A pressure cuff, for example, may be configured to measure the blood pressure of a patient and to communicate the measured values at regular intervals to a blood treatment apparatus. In order for the pressure cuff to operate, full-fledged I/O components are typically not required, except few simple components such as start/stop, on/off, reset, or similar buttons, and/or some indicators (e.g. lamps, LEDs, etc.) indicating an operating status of the pressure cuff.

A data acquisition unit may operate with or without the above-mentioned I/O components. In one example, a data acquisition unit is based on a conventional optical code reader typically comprising a suitable optical scanner configured to scan optical patterns such as bar codes or QR codes. The optical reader does not necessarily require the above-mentioned I/O components since the optical scanner may be used as an input device and the reader may be configured for use without an output device (e.g. in terms of a user interface). In this example, the optical reader may read configuration data in the form of a QR code displayed on a blood treatment apparatus, decode the configuration data, and establish a wireless communication with the blood treatment apparatus based on the decoded configuration data. Subsequently the optical reader is operably linked to the blood treatment apparatus and ready to acquire operation data to be provided to the blood treatment apparatus, typically until a pre-defined idle time is exceeded or until the optical reader is operably linked to a different blood treatment apparatus.

In another example, the data acquisition unit is based on a smart phone comprising a touch screen display as an I/O component (e.g. in terms of a user interface) as well as a camera. A data acquisition unit of this latter type may be configured (e.g. through a suitable computer software program) to provide similar functions as the aforementioned optical reader. A suitable software component may configure the camera to continuously provide images of potential optical patterns to be detected, such as QR or bar codes. Typically, the software continuously analyses the images provided by the camera and algorithms detect and decode any optical patterns included therein, for example a QR code displayed on the user interface of a blood treatment apparatus (see above).

Of course, the camera (and the relative software) may be selectively activated by the user; e.g. following pressure on a specific on/off button—either a physical button or an image on the touch screen. Alternatively, the smart phone may be equipped with NFC technology so as to communicate by proximity with the fluid processing medical apparatus, particularly with a corresponding NFC device included in the medical apparatus. The smart phone device may then establish a wireless communication with the blood treatment apparatus based on the decoded configuration data. Subsequently the smart phone device is operably linked to the blood treatment apparatus and ready to acquire operation data to be provided to the blood treatment apparatus, typically until a pre-defined idle time is exceeded or until the smart phone device is operably linked to a different blood treatment apparatus. A distinctive advantage of this latter example is that conventional and common hardware (e.g. generally inexpensive) may be used in connection with a suitable software component adapted to the individual application. Furthermore, in some examples, the smart phone devices may be provided by the medical personnel, for example if a respective user already owns a suitable smart phone device.

In cases where medical accessories lack I/O components providing input means allowing for the necessary input of configuration data in order to establish a wireless operating communication, the above-described processes and devices facilitate quick and easy setup of wireless communication.

Therefore, a mechanism is also required that allows for an easy, safe, and efficient way to establish a wireless operating communication between a medical accessory and a medical device, such as a blood treatment apparatus.

SUMMARY OF THE INVENTION

It is an object of the invention to provide a mechanism that allows for an easy, safe, and efficient way to establish a wireless operating communication between a medical accessory and a medical device.

An auxiliary object is that of providing a mechanism that allows medical accessories to temporarily establish and close a wireless operating communication with a number of medical apparatus in a quick, easy, and reliable manner, thereby allowing the medical accessories to be wirelessly linked in succession to a plurality of medical apparatus, minimizing idle time of the respective medical accessory and/or the medical apparatus.

Another auxiliary object is that of providing a mechanism that ensures that a wireless operating communication is established only between the medical accessory and the medical device that are intended for connection with each other.

At least one of the above objects is substantially achieved by a method for providing operation data to a blood treatment apparatus using a data acquisition unit, a data acquisition unit, and a system comprising a blood treatment apparatus and a data acquisition unit.

Aspects of the invention are disclosed in the following.

In accordance with a $1^{st}$ independent aspect, a method for providing operation data to a fluid processing medical apparatus is provided comprising the steps of providing the medical apparatus with a readable element; acquiring configuration data associated to the readable element of the medical apparatus by relatively approaching a data acquisition unit of a medical accessory and the readable element of the medical apparatus; establishing a wireless communication between medical accessory and the medical apparatus based on the configuration data; providing a medical component having a readable element; acquiring operation data associated to the readable element of the medical component by relatively approaching the data acquisition unit of the medical accessory and the readable element of the medical component, the medical component being destined to be operatively coupled to the medical apparatus; and providing the operation data to the medical apparatus using the wireless communication.

In accordance with a $2^{nd}$ independent aspect, a medical accessory is provided comprising a data acquisition unit, comprising: a near field communication reader configured to read data from a near field communication transmitter and receiver, or an optical reader, in particular a bar-code reader or a matrix code reader, configured to scan an optical pattern, in particular an optical bar-code or an optical matrix code; a medical accessory control unit, the medical accessory control unit being programmed to perform the steps of acquiring configuration data associated to a readable element of a medical apparatus upon the data acquisition unit and the readable element of the medical apparatus being relatively approached to one another; establishing a wireless communication between the medical accessory and the medical apparatus based on the configuration data; acquiring operation data associated to a medical component upon the data acquisition unit and a readable element of a medical component being relatively approached to one another, the medical component being destined to be operatively coupled to the medical apparatus; and providing the operation data to the medical apparatus using the wireless communication.

In accordance with a further independent aspect, a method for providing operation data to a fluid processing medical apparatus is provided comprising the steps of providing the medical apparatus with a readable element; acquiring configuration data associated to the readable element of the medical apparatus by relatively approaching a data acquisition unit of a medical accessory and the readable element of the medical apparatus; establishing a wireless communication between medical accessory and the medical apparatus based on the configuration data; providing an ID support (or card) having a readable element; acquiring operator data associated to the readable element of the ID support by relatively approaching the data acquisition unit of the medical accessory and the readable element of the ID support; providing the operator data to the medical apparatus using the wireless communication; acting on the fluid processing medical apparatus to change an operation mode of the medical apparatus, the operation mode being for example a treatment protocol, or a drug infusion, or a component substitution, or an action following an alarm, or the medical apparatus reading for subsequent use; a control unit of the fluid processing medical apparatus memorizing the operator data associated to operation mode change data.

In a $3^{rd}$ aspect according to anyone of the previous aspects, the medical accessory is a mobile communications device, optionally the data acquisition unit is a mobile phone.

In a $4^{th}$ independent aspect, a medical system is provided comprising at least a medical apparatus and at least a medical accessory according to anyone of aspects 2 to 3, the medical apparatus comprising a readable element containing at least configuration data, said configuration data allowing establishing a wireless communication between medical accessory and the medical apparatus.

In a $5^{th}$ aspect according to anyone of the previous aspects, the step of establishing the wireless communication further comprises the steps of determining, based on the configuration data, communication data of the medical apparatus, the communication data of the medical apparatus being configured for operation with the wireless communication, the communication data further being indicative of a communication configuration of the medical apparatus; initiating, based on the communication data, a data communication between the medical apparatus and the data acquisition through the wireless communication.

In a $6^{th}$ aspect according to anyone of the previous aspects, the method further comprises operatively coupling the medical component to the medical apparatus.

In a $7^{th}$ aspect according to anyone of the previous aspects, after the wireless communication has been established, the method further comprises the steps of comparing an idle time interval indicative of a time interval since the last data communication between the medical apparatus and the medical accessory using the wireless communication with a pre-defined maximum idle time interval; and closing the wireless communication if the idle time interval is greater than the pre-defined maximum idle time interval; alternatively (or in combination), after the wireless communication has been established, the method further comprises the steps of receiving a closing command form either the medical apparatus or the medical accessory; and closing the wireless communication; alternatively (or in combination), after the wireless communication has been established, the method further comprises the steps of receiving a closing command form the user acting either on the medical apparatus or on the medical accessory; and closing the wireless communication.

In a $8^{th}$ aspect according to anyone of the previous aspects, the method further comprises the step of performing an alarm procedure if the idle time interval is greater than the pre-defined maximum idle time interval.

In a $9^{th}$ aspect according to anyone of the previous aspects, after the wireless operating communication has been established, the method further comprises the steps of providing a second medical apparatus with a readable element; acquiring second configuration data associated to the readable element of the second medical apparatus by relatively approaching the data acquisition unit of the medical accessory and the readable element of the second medical apparatus; closing the wireless communication between the medical accessory and the medical apparatus; establishing a second wireless communication between the medical accessory and the second medical apparatus based on the second configuration data.

In a 10$^{th}$ aspect according to anyone of the previous aspects, the method further comprises the step of closing the wireless communication after the operation data has been provided, particularly the wireless communication being closed upon action of the medical apparatus after verifying completion of apparatus dressing with medical components.

In a 11$^{th}$ aspect according to anyone of the previous aspects, acquiring configuration data associated to the readable element comprises detecting the presence of the readable element within a maximum operating distance to the data acquisition unit of the medical accessory.

In a 12$^{th}$ aspect according to anyone of the previous aspects, the readable element of the medical apparatus and/or the readable element of the medical component comprises an optical pattern, in particular an optical bar-code or an optical matrix code (QR-code), and the data acquisition unit of the medical accessory comprises an optical reader, in particular a bar-code reader or a matrix code reader, configured to scan the optical pattern.

In a 13$^{th}$ aspect according to anyone of the previous aspects, the step of providing the medical apparatus with a readable element comprises displaying the optical pattern on a display unit of the medical apparatus, the display unit optionally comprising a graphical input/output unit, the graphical input/output unit optionally being a touch screen display.

In a 14$^{th}$ aspect according to anyone of the previous aspects, acquiring configuration data associated to the readable element of the medical apparatus comprises optically scanning the optical pattern using the optical reader; and decoding the configuration data from the optical pattern.

In a 15$^{th}$ aspect according to anyone of the three preceding aspects, acquiring operation data associated to the readable element of the medical component comprises optically scanning the optical pattern using the optical reader; and decoding the operation data from the optical pattern.

In a 16$^{th}$ aspect according to anyone of the previous aspects, the readable element of the medical apparatus and/or the readable element of the medical component comprises a near field communication (NFC/RFID) unit, the near field communication unit optionally comprising a near field communication transmitter and receiver, and wherein the data acquisition unit of the medical accessory comprises a near field communication reader configured to read data from the near field communication transmitter and receiver; alternatively the readable element of the medical apparatus and/or the readable element of the medical component comprises Bluetooth unit, the Bluetooth unit optionally comprising a transmitter and receiver, and wherein the data acquisition unit of the medical accessory comprises a reader configured to read data from the Bluetooth transmitter and receiver, the Bluetooth unit being for example a class 3 unit.

In a 17$^{th}$ aspect according to the previous aspect, acquiring configuration data associated to the readable element of the medical apparatus comprises sending an electromagnetic signal from the data acquisition unit of the medical accessory to the readable element of the medical apparatus, the electromagnetic signal optionally being sent in order to supply energy to a transponder or transceiver comprised in the readable element; receiving the configuration data in response to the electromagnetic signal and through an electromagnetic response signal; and decoding the configuration data from the electromagnetic response signal.

In a 18$^{th}$ aspect according to the previous aspect, acquiring operation data associated to the readable element of the medical component comprises sending an electromagnetic signal from the data acquisition unit of the medical accessory to the readable element of the medical component, the electromagnetic signal optionally being sent in order to supply energy to a transponder or transceiver comprised in the readable element; receiving the operation data in response to the electromagnetic signal and through an electromagnetic response signal; and decoding the operation data from the electromagnetic response signal.

In a 19$^{th}$ aspect according to anyone of the previous aspects, the method further comprises operatively coupling the medical component to the medical apparatus.

In a 20$^{th}$ aspect according to anyone of the previous aspects, the configuration data comprise one or more of identification data comprising a unique identifier associated to the medical apparatus, and wherein the step of establishing the wireless communication between the medical accessory and the medical apparatus is based on the unique identifier; type data indicative of one or more properties of the medical apparatus, optionally wherein the one or more properties of the medical accessory that the type data are indicative of, comprise one or more of hardware data indicative of a hardware configuration of the medical accessory; software data indicative of a software configuration of the medical accessory; and firmware data indicative of a firmware configuration of the medical accessory, and the step of establishing the wireless communication between the medical accessory and the medical apparatus comprises determining whether the medical apparatus is of a type suitable for operation with the medical accessory based on one or more of the hardware data, the software data, and the firmware data; status data indicative of an operating configuration of the medical apparatus, and wherein the step of establishing the wireless communication between the medical accessory and the medical apparatus comprises determining, based on the status data, whether the medical apparatus is in a status configured for operation with the medical component.

In a 21$^{st}$ aspect according to anyone of the previous aspects, the step of acquiring the configuration data further comprises determining a validity of the configuration data and, if the medical accessory determines the configuration data to be invalid, preventing the wireless communication from being established.

In a 22$^{nd}$ aspect according to the previous aspect, determining the validity of the configuration data comprises determining the configuration data to be invalid if no configuration data have been acquired; the configuration data acquired are incomplete; and/or a generated checksum computed based on the configuration data differs from a received checksum being received as a portion of the configuration data.

In a 23$^{rd}$ aspect according to anyone of the previous aspects, the method further comprises determining a validity of the operation data; and signaling, if the validity of the operation data cannot be determined.

In a 24$^{th}$ aspect according to the previous aspect, determining the validity of the operation data comprises determining the operation data to be invalid if no operation data have been acquired; the operation data acquired are incomplete; a generated checksum computed based on the operation data differs from a received checksum being received as a portion of the operation data; an operating medical component is already operatively coupled to the medical apparatus and the operating medical component and the medical component are of a same type; and/or the medical component is not configured to be operatively coupled to the medical apparatus.

In a 25$^{th}$ aspect according to anyone of the previous aspects, the medical apparatus is a blood treatment device, particularly an extracorporeal blood treatment device.

In a 26$^{th}$ aspect according to the previous aspect, the blood treatment device is configured for receiving a disposable blood circuit, the disposable blood circuit optionally including a venous line, an arterial line, and a blood treatment unit, the blood treatment unit optionally being a filter.

In a 27$^{th}$ aspect according to the two preceding aspects, the medical apparatus comprises a support structure for receiving a plurality of replaceable components of different categories in correspondence of respective operating areas of said medical apparatus, wherein said replaceable components comprise a plurality of components of different categories, each component of a same category having respective mechanical connection to a corresponding operating area on the medical apparatus, different from that of components of other categories and wherein said medical apparatus includes a plurality of different types of engaging means, each type of engaging means being designed for mechanically engaging, in a respective operating area, a component of one corresponding category only.

In a 28$^{th}$ aspect according to the previous aspect, the replaceable components of different categories include filters, concentrate cartridges, and bloodlines.

In a 29$^{th}$ aspect according to anyone of the previous aspects, the method further comprises the steps of providing a new medical component having a readable element; acquiring new operation data associated to the readable element of the new medical component by relatively approaching the medical accessory and the readable element of the new medical component; providing the new operation data to the medical apparatus using the wireless communication; operatively coupling the new medical component to the medical apparatus; optionally wherein the above steps are repeated for each new medical component of a plurality of new medical components.

In a 30$^{th}$ aspect according to anyone of the previous aspects, the method further comprising the steps of providing an additional medical component having a readable element; acquiring additional operation data associated to the readable element of the additional medical component by relatively approaching the medical accessory and the readable element of the additional medical component; providing the additional operation data to the medical apparatus using the wireless communication; operatively coupling the additional medical component to the medical apparatus; optionally wherein the above steps are repeated for each additional medical component of a plurality of additional medical components.

According to a 31$^{st}$ independent aspect, a method for setting up a fluid processing medical apparatus is provided, the method comprises the steps of providing the medical apparatus with a readable element; acquiring configuration data associated to the readable element of the medical apparatus by relatively approaching a data acquisition unit of a medical accessory and the readable element of the medical apparatus; establishing a wireless communication between the medical accessory and the medical apparatus based on the configuration data; providing a first medical component having a readable element; acquiring first operation data associated to the readable element of the first medical component by relatively approaching the data acquisition unit of the medical accessory and the readable element of the first medical component; providing the first operation data to the medical apparatus using the wireless communication and operatively coupling the first medical component to the medical apparatus; providing a second medical component having a readable element; acquiring second operation data associated to the readable element of the second medical component by relatively approaching the data acquisition unit of the medical accessory and the readable element of the second medical component; providing the second operation data to the medical apparatus using the wireless communication and operatively coupling the second medical component to the medical apparatus.

In a 32$^{nd}$ aspect according to the previous aspect, the first medical component and the second medical component are of different medical component categories.

In a 33$^{rd}$ aspect according to anyone of the previous aspects, the steps are performed by a medical apparatus control unit or by a medical accessory control unit of the medical accessory.

In a 34$^{th}$ aspect according to anyone of the previous aspects, the operation data includes at least one or more data selected in the group comprising identity of the medical component, identity of a series of identical medical components, expiration date of the medical component, manufacturer of the medical component, one or more commands for programming the medical apparatus to execute a procedure on the fluid, data concerning a patient.

In a 35$^{th}$ aspect according to anyone of the previous aspects, the fluid processing medical apparatus is an infusion pump.

In a 36$^{th}$ aspect according to the previous aspect, the infusion pump includes a main body portion, a display contained on the main body portion for displaying user interface information; at least one pump module secured to the main body portion and adapted to receive a tube, the pump module having means for applying pumping action to the tube; and a pump control unit associated to the main body portion for generating user interface information on the display areas.

In a 37$^{th}$ aspect according to anyone of the previous aspects, the medical component is a disposable component chosen in the group including bags, concentrates, filters, blood lines, syringes, cassettes.

In a 38$^{th}$ aspect according to anyone of the previous aspects, the medical component is a semi-permanent medical component to be connected to the fluid processing medical apparatus, such as a ultrafilter for dialysate side to be substituted after a plurality of medical treatments.

In a 39$^{th}$ aspect according to anyone of the previous aspects, the medical component is a permanent medical component to be connected to the fluid processing medical apparatus, such as a pump, a pump module and/or a non-disposable tubing for dialysate.

In a 40$^{th}$ aspect according to anyone of the previous aspects, the medical component has a wireless communication unit, once operation data are provided to the medical apparatus by the medical accessory, the medical component wireless communicating directly with the fluid processing medical apparatus.

In a 41$^{st}$ aspect according to anyone of the previous aspects, the data acquisition unit of the medical accessory includes at least two readers of different nature, such as an optical and a near field reader.

In a 42$^{nd}$ aspect according to anyone of the previous aspects, the method further includes the step of removing a medical component, said step of removing includes one of the following sub-steps: reading a second time the same medical component, manually starting a removal procedure on a user interface of the medical apparatus or of the medical accessory, reading a second medical component of the same category of a component already read.

DESCRIPTION OF THE DRAWINGS

The following drawings relating to aspects of the invention are provided by way of non-limiting example:

FIG. 7 shows the process of providing operation data to a blood treatment apparatus using a data acquisition unit according to Example 1, FIG. 8 schematically shows an RFID unit in the form of an RFID tag that may be integrated into a medical apparatus and/or medical accessory.

DETAILED DESCRIPTION

Figure 1:
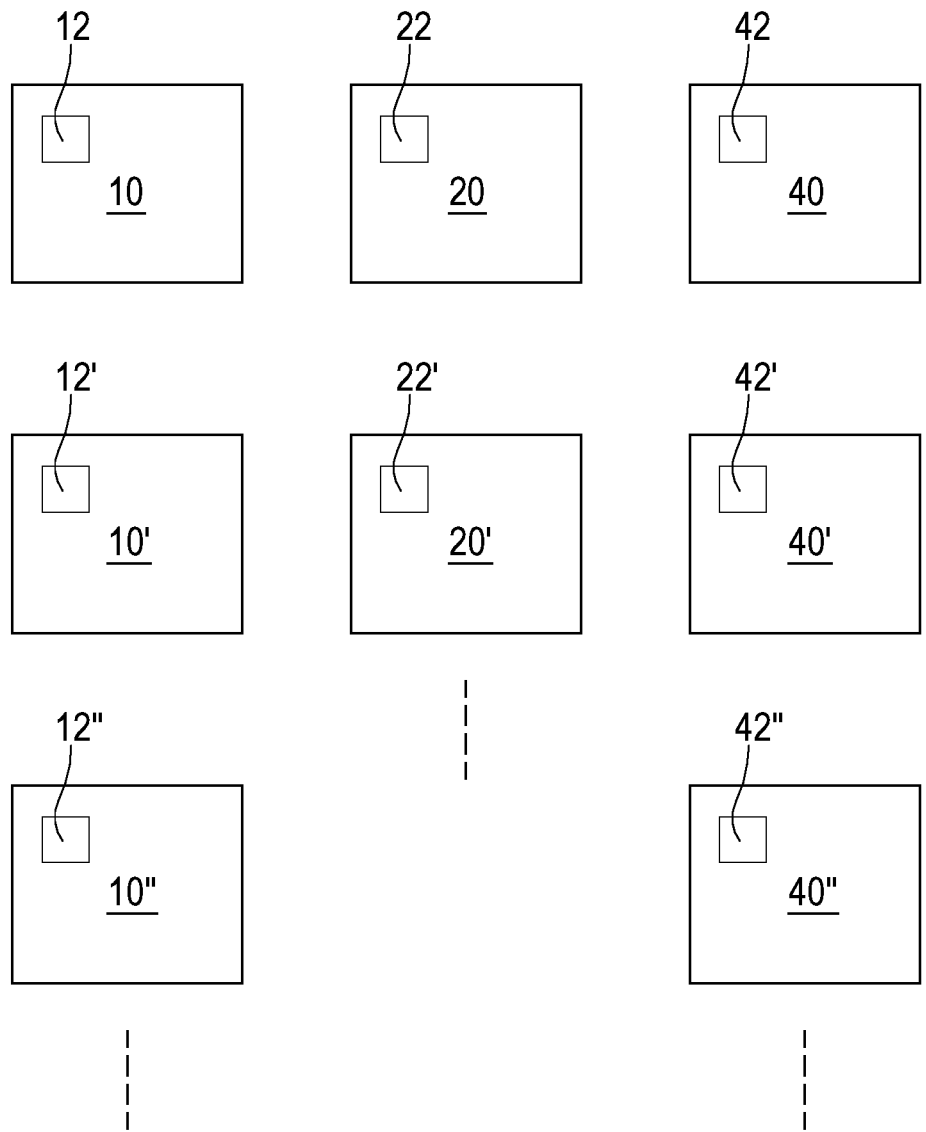
FIG. 1 shows a schematic representation of medical apparatus, medical accessories, and medical components.

With reference to the following description, a readable element may store certain data and provide these data to be acquired by a suitable reading means. A readable element provided at or associated to a medical apparatus may store configuration data for the purpose of establishing a wireless communication with the medical apparatus. A readable element provided at or associated to a medical component may store operation data for the purpose of determining whether the medical component may be operably coupled to the medical apparatus. A readable element may be configured to store data of different size and to provide these data in different ways (e.g. based on optical or electromagnetic means). The readable element may provide data accessible using a low range and/or low bandwidth communication, for example requiring close proximity of the communicating entities or units. In particular, the data may be accessible using a unidirectional communication. In particular, the data may be accessible using a bi-directional communication.

In terms of more abstract concepts, accessing data stored in the readable element may be achieved by a data acquisition unit using an auxiliary wireless communication. Therefore, acquiring configuration data associated to the readable element may be regarded as involving a wireless auxiliary communication. This term is used in order to clarify that this auxiliary wireless communication may be used to establish a wireless communication that is subsequently used to transfer operating data (i.e. bulk data of any kind required for operating the medical apparatus and/or the medical accessory). In some embodiments, the wireless auxiliary communication may be based on the same communication components and/or standards as the wireless communication established between the medical apparatus and the medical accessory. In other embodiments, the communication components and/or standards may be different from one another.

In some embodiments, the readable element comprises an optically detectable pattern (e.g. a bar code or a QR code) in which data is encoded. Reading the data encoded in the optical pattern involves scanning the optical pattern, which is an entirely wireless process. In other embodiments, the readable element may additionally or alternatively comprise an electromagnetically readable unit (e.g. an RFID tag) in which data is stored. Reading the data stored in the readable unit involves receiving electromagnetic signals emitted from the readable unit.

Generally, in some examples, the wireless auxiliary communication is realized using optical means, in which an optical scanner (i.e. the data acquisition unit) detects an optical element present in the vicinity of the scanner. For example, the medical apparatus may have an optical pattern (e.g. bar-code or QR-code) affixed thereto and configured for detection by an optical scanner comprised in the medical accessory. Upon bringing the medical accessory into the proximity of the medical apparatus (e.g. a blood treatment apparatus or an infusion pump)—more precisely, upon bringing the optical scanner of the medical accessory into the proximity of a readable element associated to the medical apparatus, so that the optical scanner of the medical accessory may detect and scan the optical pattern, the data encoded in the optical pattern may be scanned and decoded by the medical accessory. In this example, the readable element of the medical apparatus is the optical pattern having data encoded therein, and the data acquisition unit comprises an optical scanner configured to scan and, optionally, to decode the optical pattern. For a detection to be possible, the distance between the medical accessory and the medical apparatus (more precisely, between the optical pattern and the optical scanner, i.e. between the readable element and the data acquisition unit) is typically 2 m or less. In some examples, the distance may be 1 m or less, or even 50 cm or less. In general, the optical scanner and the optical pattern may be configured to facilitate detection and scanning at any desired distance within the optical limitations for optical scanning equipment, for example by adapting the size of the optical pattern and/or providing the optical scanner with one or more suitable light sources, optical lenses, or other optical components required for scanning at the desired distance. For example, a larger optical pattern and/or a longer focal length may facilitate detection from a farther distance.

In one example, a QR-code is used. The data capacity of a QR-code depends on its version number and the level of error correction. The data capacity ranges from about 10 (version 1) to about 4.000 (version 40) alphanumeric characters. A QR-code has error correction capability to restore data if the code cannot be scanned entirely correctly, for example due to optical effects or wear of the original pattern.

Four error correction levels L, M, Q, and H are available, offering error correction from about 7% (level "L") to about 30% (level "H") of total code words (one code word being equal to 8 bits of information). The maximum distance at which a QR-code may be reliably read depends on technical (e.g. optical properties of the scanner, the size and/or version of the QR-code pattern, etc.) and external factors (e.g. lighting conditions). Typically, the maximum reading distance is about 10 times the size of the QR-code (e.g. for version 2 QR-codes). In one example, if the (version 2) QR-code has a size of 25 mm×25 mm, the maximum reading distance is about 25 cm. The desired maximum reading distance may, thus, easily be pre-determined by reducing or enlarging the size of the QR-code to be read, taking into account the technical properties of the optical scanners intended for use with the QR-code.

It is understood that any optical pattern that may be detected, scanned, and read by suitable detecting, scanning, and decoding equipment may be used within the scope of the present invention, as long as the respective data may be encoded within the pattern and the pattern may be scanned and decoded. In some examples, a simple (e.g. one dimensional) bar code having few a few Bytes of data encoded therein is sufficient to store, for example, a numerical ID. In other examples, more complex one- or two-dimensional codes may have a capacity of many Kbytes. Additional "dimensions" may include, for example, color coding. The respective capacity may be chosen based on the individual requirements of the application.

One advantage of using an optical pattern is that if the medical apparatus includes a suitable user interface (e.g. a touch screen or similar), then the optical pattern may be displayed on the user interface whenever required, without necessitating providing the medical apparatus with a permanent pattern (e.g. a printed sticker affixed to the apparatus). In this example, the optical pattern generated by the medical apparatus and displayed on the user interface thereof may be dynamically generated in order to reflect current properties of the medical apparatus and/or to convey any other relevant data that varies over time.

In other examples, the wireless auxiliary communication is realized using electromagnetic communication means, in which a transmitter sends out an electromagnetic signal that may be received by a receiver. For example, the medical accessory may have a near field communication (NFC) unit (e.g. RFID code or suitable transmitter/receiver) associated thereto and configured for communication with a corresponding NFC unit associated to the medical apparatus. Upon bringing the medical accessory into the proximity of the medical apparatus (more precisely, upon bringing the data acquisition unit in the form of an electromagnetic reader of the medical accessory into the proximity of the readable element of the blood treatment apparatus/infusion pump), so that the NFC unit of the medical accessory may detect and receive signals from the NFC unit of the medical apparatus, the data encoded in the transferred signal may be received and decoded by the medical accessory. In this example, the data storage unit is the NFC unit (e.g. RFID tag; active or passive) of the or of the infusion pump treatment apparatus, and the electromagnetic reader is the NFC unit (e.g. RFID reader) of the medical accessory. For a detection to be possible, the distance between the readable element of the medical apparatus and the data acquisition unit of the medical accessory (i.e., between the two NFC units and/or their components, e.g. antennae, sensors, transceivers, etc.) is typically 2 m or less. In some examples, the distance may be 20 cm or less, or even 10 cm or less. In general, the NFC units may be configured to facilitate detection and reading at any desired distance within the designed operating range of NFC units.

With reference to the following description, a wireless communication provides data communication for the purpose of transferring bulk data (e.g. operation data, medical data, treatment relevant data, etc.) necessary for setup or operation of the medical apparatus. Typically, the medical accessory comprises a data acquisition unit configured to acquire data from readable elements associated to medical apparatus and/or medical components using the aforementioned auxiliary wireless communication (e.g. optical scanning, NFC, Bluetooth, etc.). The medical accessory is further configured to provide any data acquired to the medical apparatus using a wireless communication established between the medical accessory and the medical apparatus. The wireless communication may be a medium to long range and/or medium to high bandwidth wireless communication. In particular, the wireless communication may be a bi-directional wireless communication. In some examples and/or for specific applications, the wireless communication may be a unidirectional communication.

With reference to the appended drawings, FIG. 1 shows a schematic representation of medical apparatus, medical accessories, and medical components. Generally, medical apparatus 10 (10', 10", etc.) is provided with a readable element 12 (12', 12", etc.) configured to store data, in particular configuration data required for establishing a wireless communication with the respective medical apparatus.

Medical accessory 20 (20', etc.) comprises a data acquisition unit 22 (22', etc.) configured to read data stored and provided by readable elements 12, 12', 12", etc. It is noted that the number of medical accessories does not have to correspond to the number of medical apparatus. Typically, there is a 1:n relationship between the number of medical accessories and the number of medical apparatus. Therefore, the number of medical accessories may be beneficially reduced when any one medical accessory is temporarily linked in sequence to a number of medical apparatus, wherein the wireless communication between any pair of medical accessory and medical apparatus is established only for limited periods of time, thereby facilitating the use of one medical accessory with a plurality of medical apparatus in succession. As illustrated, this setup eliminates the requirement of having one medical accessory fixedly associated to one medical apparatus.

Medical component 40 (40', 40", etc.) is provided with a readable element 42 (42', 42", etc.) configured to store data, in particular operation data required in connection with operably coupling the medical component to a medical apparatus. The operation data may be read by a medical accessory in wireless communication with the medical apparatus, to which the medical component is intended to be operably coupled. Upon providing the operation data to the medical apparatus, the data may be checked for compliance with technical properties of the medical apparatus and/or requirements of the treatment to be performed and, if all requirements are met, a user may be provided with a signal indicating that the medical component is cleared for being operably coupled to the medical apparatus.

Figure 2A:
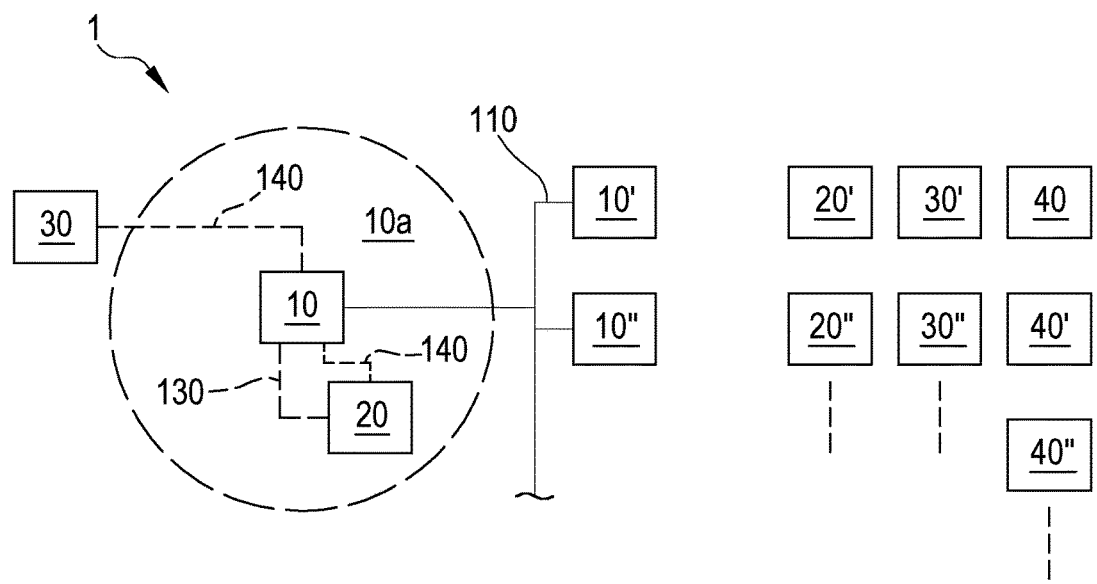
FIG. 2A shows an example network infrastructure, in which the process for providing operation data to a medical apparatus using a medical accessory in accordance with the invention may be employed.

FIG. 2A shows an example network infrastructure, in which the process for providing operation data to a blood treatment apparatus using a medical accessory in accordance with the invention may be employed. A system 1 generally comprises one or more fluid processing medical apparatus (e.g. treatment apparatus or infusion pump) 10, 10', 10", etc.

and one or more medical accessories 20, 20', 20", etc. The blood treatment apparatus 10, 10', 10" may be in data communication using a wired network 110. Alternatively (not illustrated), blood treatment apparatus 10, 10', 10" may be in data communication using a wireless network 120. It is noted that for reasons of clarity, FIG. 2A shows a number of apparatus 10, 10', 10" and accessories 20, 20', 20". However, as described above, there generally is a 1:n relationship between the number of apparatus 10 and accessories 20 wherein one accessory may be configured to be operably linked to an apparatus for short periods of time only during which a link is required, so that a single accessory 20 may be used in combination with a number of apparatus 10. Medical accessories 20, 20', etc. comprise respective data acquisition units 22, 22', etc., which are not shown in all drawings for reasons of clarity (cf. FIG. 1). The same applies to readable elements 12, 12', 12", 42, 42', 42", etc. of medical apparatus 10, 10', 10", etc. and medical components 40, 40', 40", etc.

Proximity to medical apparatus 10 is illustrated by dashed line 10a, wherein medical accessory 20 within dashed line 10a is regarded as being in proximity to medical apparatus 10. It is noted that this concept of proximity is purely an abstract concept, very much depending upon the properties of the wireless auxiliary communication, which defines the concept of proximity due to its technical limitations, properties, and/or selected parameters. As described above, the proximity of the data acquisition unit of the medical accessory to the readable element of the medical apparatus is relevant here. It might, therefore, be (also) required, to orient or align the data acquisition unit with respect to the readable element in a manner that brings the data acquisition unit into the required proximity to the readable element of the apparatus required for acquiring data stored by the readable element. In one example, this may require holding the medical accessory with the data acquisition unit (e.g. the optical reader or RFID reader) in front of, close to, and/or generally facing the readable element (e.g. an optical code or RFID tag) of the medical apparatus.

For example, if the wireless auxiliary communication is based on optical pattern scanning (see above), then the proximity to a blood treatment apparatus 10 may be defined as a portion of space relative to the optical scanner 22 (i.e. the data acquisition unit) of medical accessory 20, in which the optical scanner 22 may detect and scan an optical pattern 12 (i.e. the readable element) present on blood treatment apparatus 10. In this example, the portion of space may have a frustoconical shape situated in front of optical scanner 22 of medical accessory 20.

In another example, if the wireless auxiliary communication is based on NFC (see above), then the proximity to a blood treatment apparatus 10 may be defined as a portion of space relative to an NFC unit 22 (i.e. the data acquisition unit) of medical accessory 20, in which the NFC unit 22 may detect the presence of an NFC unit 12 (i.e. the readable element) of blood treatment apparatus 10 and receive an electromagnetic signal transmitted therefrom. In this example, the portion of space may have a substantially spherical shape situated around the NFC unit 22 of medical accessory 20.

In general, relatively approaching the data acquisition unit 22 of the medical accessory and the readable element 12 of the medical apparatus may include relatively positioning the data acquisition unit 22 and/or the readable element 12 so that data encoded in the readable element 12 of the medical apparatus 10 may be acquired by the data acquisition unit 22 of the medical accessory.

In FIG. 2A, the proximity to blood treatment apparatus 10 is illustrated by dashed line 10a denoting a spherical portion of space around device 10. As shown, establishing a wireless auxiliary communication between device 10 and accessory 20 is possible, since medical accessory 20 is shown in proximity of device 10 (i.e. within dashed line 10a). Accessories 20' and 20" however, currently cannot establish a wireless auxiliary communication with device 10, because accessories 20' and 20" are located too far away from device 10, thereby being outside the maximum operating distance of the wireless auxiliary communication. Establishing a wireless operating communication between any of accessories 20' or 20" and device 10 would, therefore, not be possible—unless the accessories are brought into proximity of device 10. The same applies to any of the other medical apparatus 10', 10", etc. in combination with any of the medical accessories.

As shown, an auxiliary data communication 130 has been established between accessory 20 and device 10, such that configuration data stored by readable element 12 (not shown) may be read by data acquisition unit 22 (not shown) of medical accessory 20. Subsequently, a wireless communication 140 may be established as shown between accessory 20 and device 10, based on the configuration data acquired from readable element 12 through wireless auxiliary communication 130 (e.g. by scanning an optical code associated to medical apparatus 10). The wireless auxiliary communication between accessory 20 and device 10 may subsequently be closed, a state not illustrated in FIG. 2A. It is further noted that generally the accessories 20, 20', 20", etc. may be configured to connect only to a single device 10, 10', 10" at the same time. However, depending upon the properties of devices, accessories, treatments, applications, etc., it may be desirable to have exceptions to this rule. Similarly, generally the apparatus 10, 10', 10", etc. may be configured to be able to connect to only one of accessories 20, 20', 20", etc. at the same time. However, depending upon the properties of devices, accessories, treatments, applications, etc., it may be desirable to have exceptions to this rule (e.g. a device being configured to connect to multiple medical accessories at the same time).

Further, a second accessory 30 of a different type than accessory 20 is also shown as being in a wireless communication with medical apparatus 10, wherein the wireless auxiliary communication between accessory 30 and device 10 has already been closed as it is no longer required. It is noted that it may be desirable to maintain a wireless communication between an accessory 20, 20', 20", 30, 30', 30" etc. even if the accessory leaves the proximity of device 10. In some examples (e.g., when an optical pattern and optical scanner are used), it might be required to remove the medical accessory (e.g. the data acquisition unit of the medical accessory) from the proximity of the medical apparatus (e.g. the readable element of the medical apparatus) when the wireless communication has been established, because the medical accessory has to be repositioned in order to acquire operation data from one or more medical components 40, 40', 40", etc. For example, a medical accessory measuring the blood pressure of a patient has to be attached to a limb of the patient. It is understood that, upon establishing the wireless operating communication between the blood treatment apparatus, which the patient is connected to, and the medical accessory, it is no longer required for the data storage unit of the medical accessory to remain in close proximity to the data acquisition unit of the blood treatment apparatus, so that the medical accessory may be fitted to the patient and the patient may comfortably rest upon a proper support during the treatment performed by the blood treatment apparatus.

Depending upon the specific properties of the medical apparatus, medical accessory, treatment, application, etc., it may alternatively be desired to close the wireless communication 140 as soon as the accessory is no longer in proximity to the device (additionally or alternatively, an alarm procedure may be performed). FIG. 2A illustrates medical accessories 20 and 30 each being in a respective wireless communication 140 with medical apparatus 10. Additional medical accessories 30', 30", etc. and the handling thereof essentially corresponds to that of medical accessories 20, 20', 20", etc. as described above.

Figure 2B:
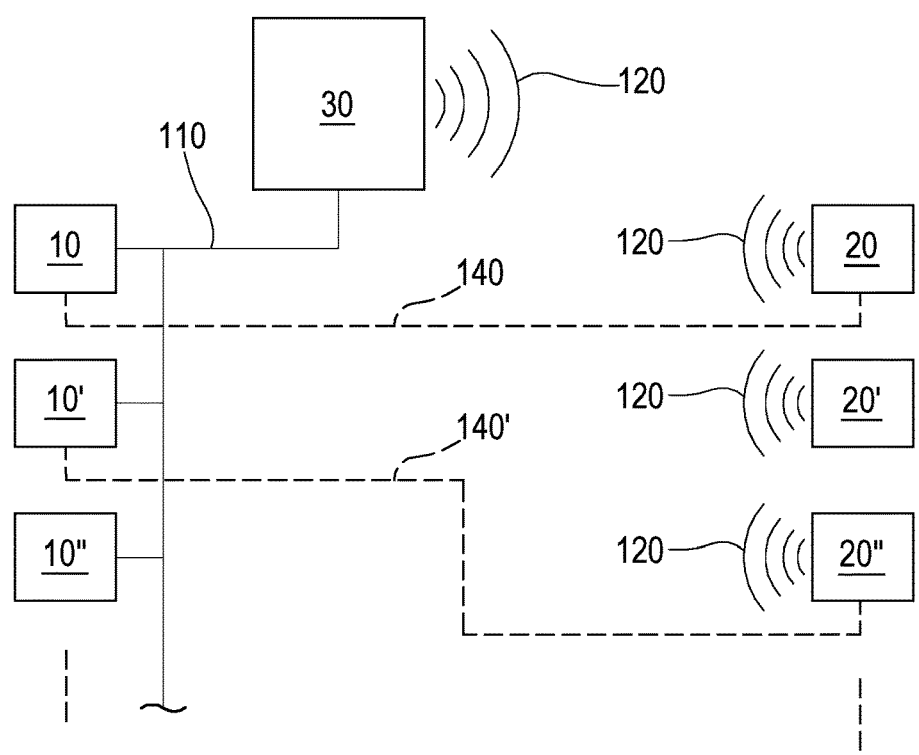
FIG. 2B shows another exemplary network infrastructure, in which the process for providing operation data to a medical apparatus using a medical accessory in accordance with the invention may be employed.

FIG. 2B shows another exemplary network infrastructure, in which the process for providing operating data to a medical apparatus using a medical accessory in accordance with the invention may be employed. FIG. 2B does not show the proximity concept around any of apparatus 10, 10', 10", etc. but focuses on the manner a wireless communication may be established. As illustrated in FIG. 2B, a number of blood treatment apparatus 10, 10', 10", etc. are associated to a wired network. Further, a wireless access point 30 or similar apparatus provides a wireless network connection 120, substantially spanning an overall network across the wired and wireless networks, effectively connecting all medical apparatus 10, 10', 10" and medical accessories 20, 20', 20" to one another. As illustrated, a wireless auxiliary communication (already closed and, therefore, not shown) between medical accessory 20 and medical apparatus 10 has facilitated establishing a wireless communication 140 between apparatus 10 and accessory 20. Apparatus 10 and accessory 20 may communicate via the wireless communication 140, which is realized through a wireless network 120 (i.e. between accessory 20 and access point 30) and further through a wired network 110 (i.e. between access point 30 and apparatus 10). The physical network connection is transparent for the wireless communication 140. In the state shown in FIG. 2B, medical accessory 20 is operably linked to medical apparatus 10. In this state, medical accessory 20 is configured to acquire operation data from medical components 40, 40', 40", etc. (not shown) and to provide these data to medical apparatus 10. In a similar manner, a wireless communication 140' has been established between accessory 20" and device 10', so that medical accessory 20" is operably linked to medical apparatus 10'. In this state, medical accessory 20" is also configured to acquire operation data from medical components 40, 40', 40", etc. (not shown) and to provide these data to medical apparatus 10'. Any of the medical accessories 10, 10', etc. may close a wireless communication established with a respective medical apparatus and establish a wireless communication with a different medical apparatus.

Figure 3:
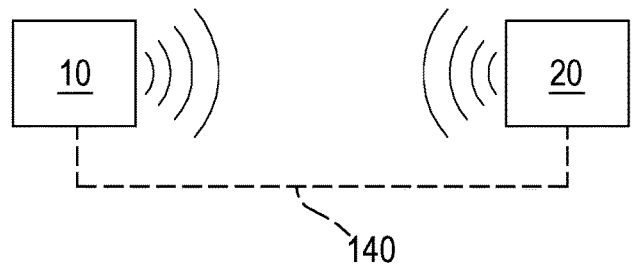
FIG. 3 shows an example of a direct communication between an apparatus 10 and an accessory 20, in which the process for providing operation data to a medical apparatus using medical accessory in accordance with the invention may be employed.

FIG. 3 shows an example of a direct wireless communication between an apparatus 10 and an accessory 20, in which the process for providing operation data to a medical apparatus using medical accessory in accordance with the invention may be employed. With reference to FIGS. 2B and 2C, it is noted that the presence of a network infrastructure 110, 120 as shown in FIG. 3 is not necessarily required. As shown in FIG. 2C, a wireless operating communication 140 between accessory 20 and apparatus 10 may also be established directly, namely without any intermediate network infrastructure, wherein apparatus 10 and accessory 20 communicate directly with one another. In one example, the direct communication between apparatus 10 and accessory 20 is realized using an ad-hoc WLAN connection.

A wireless ad-hoc network is a decentralized type of wireless network. The network is referred to as "ad-hoc" because it does not rely on an intermediate network infrastructure (e.g. including routers or access points in managed wireless networks, operating in the so-called "infrastructure" mode). Instead, each node participates in routing by forwarding data for other nodes, so that the determination of which nodes forward data is made dynamically on the basis of network connectivity. In the example shown in FIG. 3, two network devices are in data communication using an ad-hoc WLAN connection created between the two network devices, i.e. apparatus 10 and accessory 20. The wireless communication is independent from the manner in which the actual data communication between two network devices is realized, as long as the concrete realization facilitates establishing the wireless communication.

Figure 4:
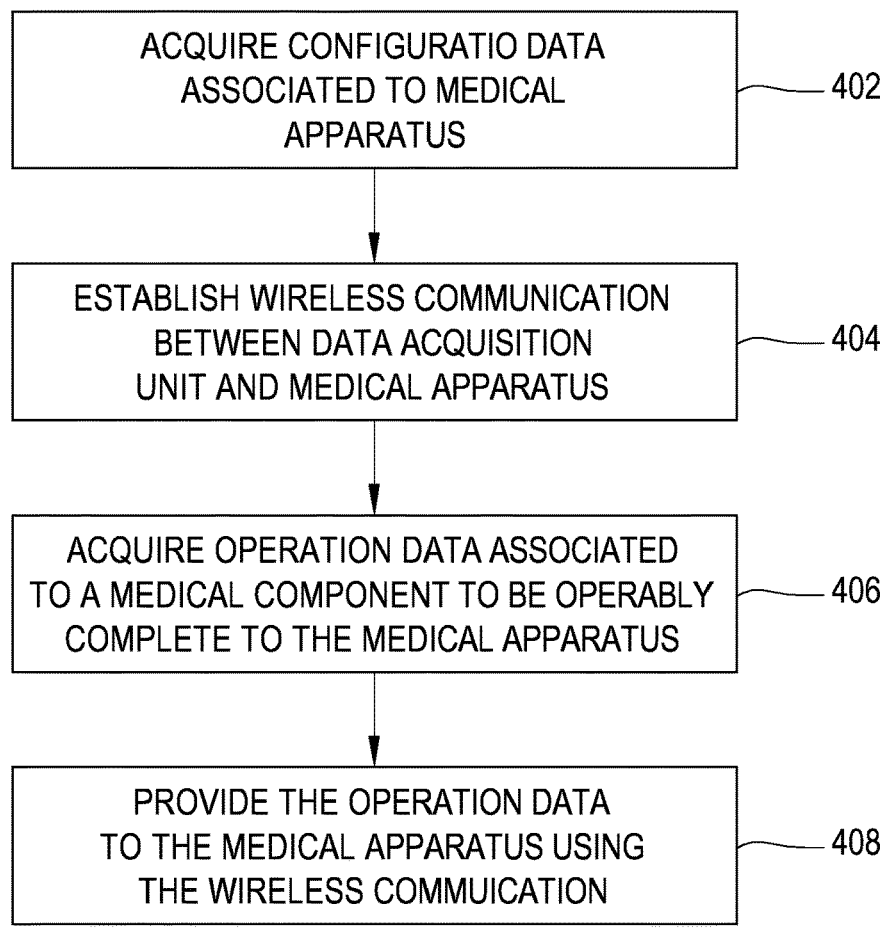
FIG. 4 is a block diagram showing the general process of providing operation data to a medical apparatus using a medical accessory.

FIG. 4 is a block diagram showing the general process of providing operation data to a medical apparatus using a medical accessory. In this example it is assumed that the medical apparatus 10 (e.g. a blood treatment device) has already been provided with a readable element 12. In step 402, the medical accessory 20 acquires configuration data stored by the readable element 12 of the medical apparatus 10 by using data acquisition unit 22. In step 404, a wireless communication is established between the medical accessory 20 and the medical apparatus 10 based on the configuration data acquired in step 402. In step 406, the medical accessory 20 acquires operation data from a readable element associated to a medical component 40 (e.g., a filter component designed to be operably coupled to medical apparatus 10). The technical manner in which the operation data are acquired may be the same as employed in acquiring the configuration data (e.g., optical pattern scanning or reading data from an RFID tag). In step 408, the medical accessory 20 provides the operation data acquired in step 406 to the medical apparatus 10 based on the wireless communication established in step 404.

The general process of establishing a wireless communication is based on the wireless auxiliary communication having a limited range that requires the accessory and device (more precisely, the readable element of the medical apparatus and the data acquisition unit of the medical accessory) to be in a pre-defined proximity or closer to each other. One motivation is to make this proximity requirement a systematic requirement that cannot easily be adjusted or overcome by locally changing configuration parameters or adapting any one of the apparatus and accessory. In contrast, it is desired that the accessory be brought into proximity to the apparatus in order to ensure that the operating personnel may physically (e.g., visually) confirm the presence of both the accessory and the apparatus, as well as their respective current status and configuration. Only if the accessory is within the pre-defined proximity of the device or closer, an attempt to establish data communication between the two entities may be initiated, because the wireless auxiliary communication is, by design, not capable of communication over distances longer than the pre-defined proximity. This is a strong requirement, which prevents users from mistakenly establishing data communication between apparatus and accessories not intended for being linked.

As such, the maximum operating distance of the wireless auxiliary communication is required to be shorter than the maximum operating distance of the wireless communication. Further, the wireless auxiliary communication has a pre-defined maximum operating distance, which is in particular configured not to be (easily) changeable by a user locally. In this manner, establishing a wireless communication between an apparatus and an accessory is only possible if the accessory is within the maximum operating distance of the wireless auxiliary communication, whereas a safe and reliable wireless connection may be achieved through the wireless communication, because the maximum operating distance thereof is (much) longer than that of the wireless auxiliary communication.

Prior to establishing a wireless communication between the medical apparatus and the medical accessory, configuration data facilitating the wireless communication have to be set. It is known that generic networking devices typically comprise I/O means, which enable a user to enter the desired configuration data manually, for example providing WLAN access credentials and other parameters. According to the described process, the configuration data are acquired using a wireless auxiliary communication, wherein the configuration data contain the necessary data (which may, in some cases, be entered manually, see above) in a manner that allows for the apparatus and accessory to establish a wireless communication between each other without further intervention of a user. Substantially at the same time of acquiring the configuration data, presence of the medical accessory in proximity of the medical apparatus is ensured, because of the proximity being required by the maximum operating distance of the wireless auxiliary communication. If the proximity requirement is not fulfilled, the auxiliary wireless communication cannot be established and no data may be acquired using the same.

In one example, the medical apparatus and the medical accessory are already in data communication with a same (wireless) data network (e.g. WLAN), without having established a data communication with each other (which would be required in order to transfer operating data between each other). In order to establish a wireless communication with each other, at least one of the apparatus 10 and accessory 20 have to be able to identify the other and parameters for establishing the communication have to be transferred. Generally, it is the medical accessory that needs to identify the medical apparatus and to acquire configuration data facilitating establishing a wireless communication between the medical accessory and the medical apparatus.

Typically, the medical apparatus provides configuration data that allows the medical accessory to establish a wireless communication with the medical apparatus and/or to determine a number of properties of the medical apparatus.

The configuration data may comprise one or more of a Service Set Identifier (SSID), a channel number (e.g. 1 to 11 or 13, depending upon region) or operating frequency (or frequency range), a pre-shared key or other parameters and/or credentials necessary for establishing a wireless communication. In one example, the medical apparatus provides one or more of the above configuration data to the medical accessory, which subsequently may establish a wireless connection to a wireless network based on the configuration data. Afterwards, a wireless communication may be established between the blood treatment apparatus and the medical accessory, both of which are then connected to the same (wireless) network and are operably linked to one another. Subsequently, the medical accessory may acquire operation data from one or more medical components and provide these operation data to the medical apparatus using the established wireless communication. This is further detailed below.

Additionally or alternatively, the configuration data may comprise an apparatus id, an apparatus type, an apparatus status, an apparatus configuration, etc. In some examples, an apparatus id and/or apparatus type may be used by the medical accessory to identify a medical apparatus and confirm that the medical apparatus, with which a wireless communication is to be established, is actually suitable for operation with the medical accessory or vice versa. In some examples, the medical accessory determines, based on an apparatus status (e.g. primed, unused, indicating proper operation, treatment parameters, patient parameters, etc.) and/or an apparatus configuration (e.g. filter unit installed, dialysis supply connected, waste container missing, etc.) in order to determine a proper status and/or configuration of the medical apparatus. In all examples, if the medical accessory determines that the medical apparatus is not of the required type or lacks the required status and/or configuration, it is possible that the medical accessory denies establishing a wireless operating communication. The same situation may arise if the medical apparatus already has a wireless communication established with another medical accessory of the same or a different type. Depending on the individual application, it may be desirable for the medical apparatus to either deny an additional wireless communication, to allow an additional wireless communication in parallel to the existing wireless communication, or to allow an additional wireless communication in place of the existing wireless communication, which is then closed prior to establishing the new wireless communication as per the additional request.

In a specific embodiment, the fluid processing medical apparatus is an infusion pump. All mentioned communication steps/protocols applies exactly to an infusion pump as well.

In detail the infusion pump may include, for example an intravenous fluid infusion pump. The pump may be clamped onto a standard IV pole. The pump includes a main body portion and at least one pump module portion. Of course, two or more pump module portions may be provided. It is contemplated the use of any number of pumping modules depending on the requirements of the pump user. Formed at the upper periphery of the main body portion a carrying handle may be present. The main body further includes a liquid crystal display (LCD) area which is used to convey various information about the pump to the user and provides for user interface with the pump. The main body includes data-entry keys for inputting prescriptions or other data. The main body portion includes a slave microprocessor which is a slave to a master microprocessor. The slave microprocessor further includes an analog-to-digital converter (A/D converter). All microprocessors include software in read-only memory (ROM) which drives the user interaction and pump-monitoring functions.

The infusion pump may include a single module which is connected to or disconnected from the main body portion.

The pump module includes module housing, an upper module plate and a lower module plate. Fastening means are provided to secure the pump module to the main body. The fastening means include a plurality of extended bolts which extend through apertures defined in the lower module plate, the module housing and the upper module plate to threaded apertures defined on the bottom of the main body. Any number of pump modules can be added to the infusion pump by utilizing the appropriate fastening means. The pump module includes a microprocessor.

The pump modules are generally standard IV tube pump modules; use of alternative pump modules employing alternative pumping technology, such as for example, syringe pump modules is however contemplated. The pump module includes a tube-loading channel into which a standard IV tube is loaded into the pump. The pump module includes an automatic tube-loading feature. Contained within the tube-loading channel is a keyed slot adapted to receive a slide clamp contained on the IV tube. The pump module includes a free-flow prevention feature.

The medical component according to the present description may be a disposable component, meaning a component which has to be substituted after each performed treatment. Examples of medical component of the disposable type includes bags for infusion, bags for dialysis or for spent liquid, concentrates, canisters, filters, blood lines, syringes, cassettes, dialyzers, hemofilters, hemodiafilters, etc.

Alternatively or additionally, the medical component may be/include a semi-permanent medical component to be connected to the fluid processing medical apparatus; in this respect semi-permanent means that the component may be used for more than one treatment and usually for a prefixed plurality of treatments or for a certain time period before necessitating a substitution.

Examples of semi-permanent components include an ultrafilter for dialysate side and/or concentrate or canister to be substituted after a plurality of medical treatments.

The medical component may be a permanent medical component to be connected to the fluid processing medical apparatus too. Permanent medical component means a component generally not requiring substitution during the machine life (unless specific failures of ageing) such as a pump, a pump module and/or a non-disposable tubing for dialysate.

It is relevant to mention that reading a disposable component is useful during machine dressing.

Vice versa reading a permanent component may be useful for managing machine maintenance.

Furthermore, it is noted that the medical accessory may also read a readable element of a laboratory analysis (e.g. a bar code on the papers with printed lab analysis outcome) or other sensible patient data thereby allowing the medical apparatus to access to the relevant lab data to be eventually used for the treatment or for displaying on the apparatus monitor for information purpose.

Additionally, the medical accessory may also read a readable element of an ID card of a nurse or a physician so that a certain operation performed on the medical apparatus (e.g. dressing of a blood treatment machine before use, infusing a specific medicament to the patient, substitution of an infusion bag, etc . . . ) is automatically linked to the subject making the operation.

In other terms, certain operation requires the subject doing the operation being registered into the apparatus. thereby the operator scans his ID card/support and then acts on the apparatus (or vice versa) avoiding the need to manually enter his data into the medical apparatus once or before making the required activity.

In the following, several typical usage scenarios for the method of providing operation data to a medical apparatus using a medical accessory are described. These examples are not limiting the scope of the disclosed method, but merely illustrate the possibilities for combining different technologies and processes.

EXAMPLE 1

In the first example, a medical accessory establishes a wireless operating communication via a LAN/WLAN network to a medical apparatus having a QR-code attached thereto. The medical apparatus (e.g. a blood treatment machine) has a wired connection to a local area network (LAN), which in turn is extended by one or more wireless access points providing a connection to the LAN to a number of WLAN devices and accessories. The medical accessory (e.g. an optical reader having a data acquisition unit) is in data communication with the LAN via a WLAN through the aforementioned one or more access points, effectively, therefore, being in potential data communication with any device connected to the LAN or WLAN. The blood treatment apparatus has an IP address (e.g. 10.129.10.18) assigned to it and the medical accessory also has an IP address (e.g. 10.129.10.16) assigned to it. The optical pattern is attached to the medical apparatus in the form of a printed QR-code. The QR-code (i.e. the readable element) comprises configuration data encoded therein and suitable for establishing a wireless communication with the blood treatment apparatus.

Figure 5:
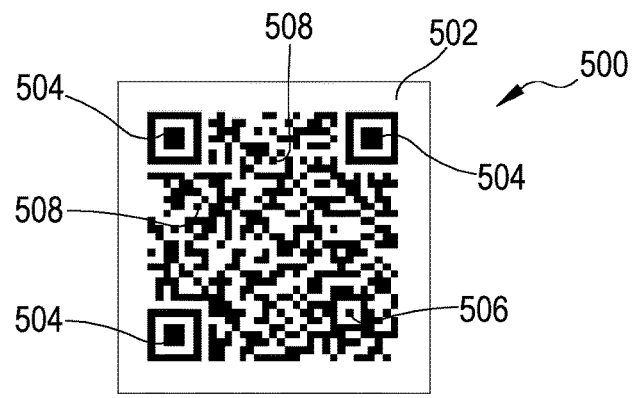
FIG. 5 shows an exemplary optical pattern, in which data, for example configuration data or operation data, may be encoded.

FIG. 5 shows an exemplary optical pattern in which data, for example configuration data or operation data, may be encoded. In Example 1, the data encoded in the QR-code is configuration data suitable for establishing a wireless communication with the medical apparatus. The configuration data encoded in the QR-code in Example 1 is (annotation added):

id=54321 (apparatus id; e.g. a numeric or text identifier)
ty=67890 (apparatus type; e.g. a numeric or text identifier)
st=101 (apparatus status; e.g. a numeric or text identifier)
cf=3 (apparatus configuration; e.g. a numeric or text identifier)
ad=10.129.10.16 (apparatus IPv4 address)
ek=6f2xCh872 (encryption key)

The QR-code shown in FIG. 5 is of the type "plain text". However, any suitable QR-code may be used to encode the configuration data. The QR-code may comprise one or more of the following elements: a "quiet" zone 502 around the QR-code, one or more finder patterns 504, one or more alignment patterns 506, timing patterns 508 running horizontally and vertically between the finder patterns (e.g. in the form of a line of alternating black and white dots running horizontally and vertically between the finder patterns), version information, data and error corrections code words, and a data encoding region.

Figure 6:
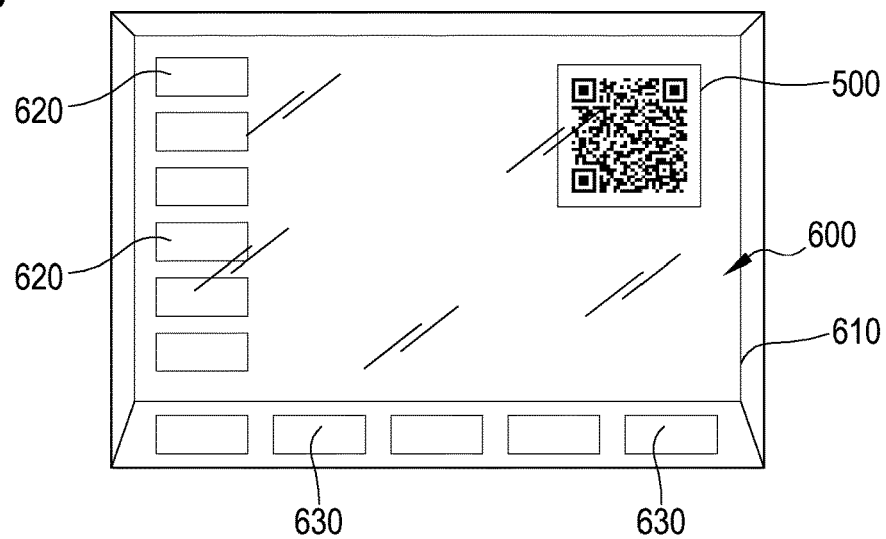
FIG. 6 shows the display of an exemplary optical pattern, in which data, for example configuration data or operation data, may be encoded, as displayed on a user interface of a medical apparatus.

FIG. 6 shows an alternative way of providing the blood treatment apparatus with a readable element. Without essentially deviating from Example 1, FIG. 6 shows a user interface 600, comprising a touch screen unit 610 and a series of input elements 620 displayed thereon. Further, the user interface 600 comprises a series of input elements 630 situated below touch screen unit 610, wherein the difference between input elements 620 and input elements 630 is, that the latter are realized as hardware buttons and the former are generated by a suitable computer software program. In this alternative of Example 1, the user interface 600 is used to display a readable element in the form of a QR-code 500 that may be substantially identical to the QR-code 500 shown in FIG. 5, except for the fact that it is not printed on a sticker and affixed to the blood treatment apparatus, but instead is displayed on the touch screen unit 610 of user interface 600.

This alternative may entail several advantages over providing the blood treatment apparatus with a permanent QR-code label (e.g. a printed sticker). For example, the QR-code 500 displayed on the touch screen unit 610 may be easily displayed upon providing suitable authentication information (e.g. a keyboard input or data read from a key card), so that another level of security is added. This would facilitate authentication and/or authorization of a user wishing to operably link a medical accessory and a medical apparatus, before configuration data is displayed and may be acquired.

Another advantage is that the contents of the encoded data may be easily changed and/or updated. While data encoded in a printed QR-code cannot be easily altered, the generated QR-code displayed on the touch screen unit may. It may, therefore, contain up to date status data regarding the medical apparatus or dynamically generated encryption data, etc.

Irrespective of the individual manner of providing the readable element in Example 1, the further process is described both covering the printed QR-code and the alternative display of a QR-code described above.

FIG. 7 shows the process of establishing a wireless operating communication between the medical apparatus and the medical accessory according to Example 1. In step 602 an operator brings the medical accessory into proximity of the blood treatment apparatus, or, more precisely, brings the data acquisition unit of the medical accessory into proximity of the readable element of the blood treatment apparatus. In this example, the optical scanner associated to the medical accessory is brought into the proximity of the QR-code attached to (or displayed on) the medical apparatus such that the optical scanner may scan the optical pattern making up the QR-code. In step 604 the optical scanner scans the optical pattern. This may be initiated either by the operator executing a scanning operation at the accessory or automatically by the accessory checking an image or representation of the scanned data supplied by the scanner at regular intervals and automatically detecting the presence of a valid optical pattern within the field of view of the scanner. The scanned image is subsequently decoded in order to attain the configuration data listed above. Optionally, an optical and/or acoustic feedback signal is given by the accessory upon completion of the scanning and/or decoding. In step 606, the medical accessory checks the configuration data. This check may be more or less extensive. First of all, a checksum (potentially present in the encoded data, but not listed above) may be computed in order to confirm the validity of the data and/or a correct scanning/decoding. Also, a plausibility check may be performed, where the configuration data are checked for any conflicting or otherwise obviously erroneous data. For example, it may be possible that the configuration data encoded in the QR-code attached to the accessory is outdated or contains implausible data. Any such problems may be checked during step 606. However, the medical accessory may check that the properties of the blood treatment apparatus, as encoded in the configuration data, indicate that the apparatus has a valid id, and is of a type, status, and configuration suitable for operation with the medical accessory. For example, even if a valid id and type are provided, the device may check if the apparatus has the correct status (e.g. all components powered up, etc.) and/or whether the apparatus has a suitable configuration (e.g. apparatus cleaned or primed, etc.). Optionally, the accessory provides an optical and/or acoustic feedback signal upon completion of checking and/or verifying the configuration data. In step 608, the accessory may check whether a functioning data connection is available. This step may, for example, include checking a TCP/IP connection between the device and the IP address of the apparatus as given in the configuration data (in Example 1, this may be done, e.g., via a network ping to the address 10.129.10.18). If the data connection is operational, the accessory may establish the wireless communication. Optionally, the accessory may provide an optical and/or acoustic feedback signal upon completion of the checking and/or establishing of the wireless communication. Step 608 may further include, for example, using the encryption key supplied by the apparatus in order to establish a secure communication (e.g. via secure sockets layer (SSL)) with the apparatus, that is tamper-proof and prevents data being changed or read by other network devices. In this context, the term "encryption key" is used to refer to all kinds of suitable data encryption mechanisms, including symmetric and asymmetric encryption, regardless of the underlying protocols and/or mechanisms. It is understood that some encryption protocols require certificates, public/private keys, etc. in order to function properly. Optionally, the accessory may provide an optical and/or acoustic feedback signal upon completion of the establishing of the wireless communication. After step 608, the wireless communication between the medical accessory and the blood treatment apparatus is established and the accessory is configured to acquire operation data from medical components and provide these operation data to the blood treatment apparatus using the wireless communication. In step 610, the medical accessory and a medical component intended to be operably coupled to the blood treatment apparatus are brought into proximity of each other. In some examples, an operator holds the medical component intended for installation (e.g. a filter unit) in one hand, and the medical accessory (e.g. the reader unit) in the other. In this example, the filter unit has a QR-code associated thereto, which may be similar to the QR-code 500 described above. The QR-code associated to the filter unit contains operation data substantially different from the configuration data described above, although the manner of storing, reading, decoding, etc. is substantially identical. The operation data encoded in the QR-code associated to the filter unit is (annotation added):

id=ABCDE (filter unit id; e.g. a unique serial number comprised of alphanumeric characters)

ty=XYZ (filter unit type; e.g. a numeric or text identifier designating the type of the filter)

cn=168 (filter unit connector; e.g. a numeric or text identifier designating a physical connector of the filter)

It is understood that the operation data may comprise any data required for checking the compliance of any of the properties of the medical component with respect to the medical apparatus and/or the treatment to be performed or any other factors relevant for the treatment. In step 612, the operation data may be decoded and checked in the same manner as described above with respect to the configuration data (see step 606). In step 614, the data are provided to the blood treatment apparatus where further processing may be performed. Typically, the blood treatment apparatus will check the operation data for compliance (see above) and provide an optical or acoustical signal to the operator indicating that the medical component is cleared for installation (or not). This signaling may entail providing installation instructions on the touch screen unit of the blood treatment apparatus, indicating to the operator how and where the medical component is to be operably coupled to the apparatus.

If multiple medical components are required for operating the blood treatment apparatus, the above steps may be repeated for each medical component.

EXAMPLE 2

In the second example, a medical accessory establishes a wireless operating communication via a LAN/WLAN network to a medical apparatus, both capable of NFC. Example 2 is similar to the above-described Example 1 in that the network infrastructure and the general process of establishing the wireless communication are practically identical, except for the technical manner in which the configuration data are transmitted.

In Example 2, the medical apparatus has an integrated RFID unit (e.g. an RFID tag or transponder) that stores the same configuration data as listed above in Example 1. An operator approaches the medical accessory to the apparatus in a similar manner as in Example 1, but focuses on getting the data acquisition unit (i.e. the NFC unit; e.g. an RFID reader) of the medical accessory into proximity to the readable element (i.e. an NFC unit; e.g. an RFID tag) integrated into or otherwise associated to the blood treatment apparatus. The accessory may automatically detect the presence of the apparatus due to the RFID unit integrated therein being activated by the RFID reader of the accessory. The RFID reader of the accessory may then read the data stored on the RFID unit integrated into the apparatus wirelessly and decode the configuration data in a suitable manner similar to the one described above.

In some examples of RFID communication, two-way radio transceivers (transmitter-receiver units) called interrogators or readers send a signal to an RFID tag and read its response. RFID tags may be passive, active or battery-assisted passive. An active tag has an on-board battery and periodically transmits its ID signal. A battery-assisted passive RFID tag has a small battery on board and is activated when in the presence of an RFID reader. A passive tag is cheaper and smaller because it has no battery. However, to start operation of passive tags, they must be initially activated with a suitable electromagnetic power level stronger than for signal transmission. The described RFID tags are suitable for the scope of the present method, as are alternative RFID and/or NFC communication components and processed. Therefore, the above description of RFID tags is not intended as limiting.

Figure 8:
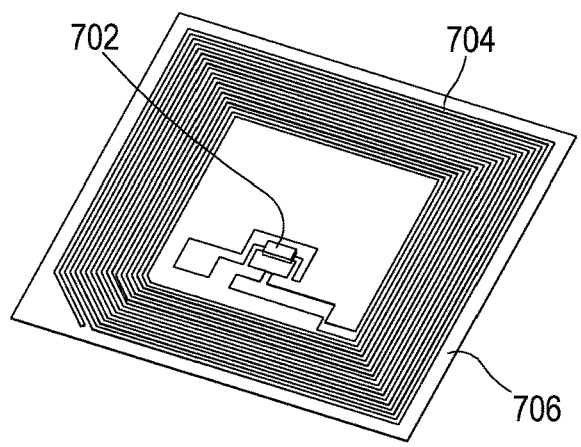

FIG. 8 schematically shows, as an example for a readable element, an RFID unit in the form of an RFID tag that may be integrated into a medical apparatus and/or medical component. The RFID tag comprises an integrated circuit or micro-chip 702 which stores the information and handles the communication with other RFID units. Further, the RFID-tag comprises an antenna 704 and a substrate 706 (e.g. an adhesive film material). The RFID tag may be integrated into the medical apparatus or component in a manner not directly visible from the outside (e.g. under a cover of some kind or generally within a housing or packaging). Alternatively, the RFID tag may be a common adhesive tag that may be affixed to an apparatus or component on an outside surface thereof, which makes it very easy to equip existing medical apparatus and components with NFC/RFID capabilities.

Except for the manner in which the configuration data and the operation data are acquired, the process steps in Example 2 are identical to those described above with respect to Example 1. It is, furthermore, noted that it is perfectly possible to utilize different technical means for different steps. For example, the medical components may be provided with a QR-code containing operation data, which may easily (and for very little cost) printed upon an outer surface of the medical components. Especially with respect to disposable or replaceable medical components this may be the most reasonable choice. The medical apparatus, however, may be provided with an RFID tag as described above, potentially storing much more data than a QR-code and being largely resistant to wear. The medical accessory may comprise several different data acquisition units, for example one for NFC and an optical reader. In this example, the medical accessory may first acquire configuration data from the apparatus using NFC and subsequently acquire operation data from the medical components using optical scanning, whereas the operation data are then provided to the apparatus using the wireless communication established between the accessory and the apparatus.

EXAMPLE 3

In the third example, a medical accessory establishes a wireless operating communication via an ad-hoc WLAN connection to a medical apparatus. In this example, the configuration data may be transferred between the medical apparatus and the medical accessory in any suitable manner (e.g. as described above with respect to Example 1 and Example 2). However, the blood treatment apparatus and the medical accessory are not connected to a common LAN/WLAN network, thus requiring an alternative means for communication. In this example, the apparatus and accessory are each equipped with a wireless communication unit capable of establishing an ad-hoc (i.e. non "infrastructure") WLAN communication which basically consists of nodes forwarding data between one another without the need for dedicated infrastructure components (e.g. routers, access points, wired networks, etc.). In order to establish an ad-hoc network, for example, the apparatus may provide the necessary network configuration including an SSID, private IP address range, etc. The accessory may then receive the corresponding configuration data from the apparatus in order establish the wireless (ad-hoc) communication. The general setup is shown in FIG. 3 as already described above.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. A method for providing operation data to a fluid processing medical apparatus, the method comprising:
   providing the medical apparatus comprising a readable element readable by at least one data acquisition unit;
   acquiring configuration data associated to the readable element of the medical apparatus by relatively approaching a data acquisition unit of a medical accessory and the readable element of the medical apparatus;
   establishing a wireless communication between the medical accessory and the medical apparatus based on the configuration data;
   providing a medical component comprising a readable element different than the readable element of the medical apparatus;
   acquiring operation data associated to the readable element of the medical component by relatively approaching the data acquisition unit of the medical accessory and the readable element of the medical component, wherein the medical component is configured to be operatively coupled to the medical apparatus; and
   providing the operation data to the medical apparatus using the wireless communication.

2. The method of claim 1, wherein establishing the wireless communication further comprises:
   determining, based on the configuration data, communication data of the medical apparatus, the communication data of the medical apparatus configured for operation with the wireless communication, wherein the communication data is indicative of a communication configuration of the medical apparatus; and initiating, based on the communication data, a data communication between the medical apparatus and the data acquisition through the wireless communication.

3. The method of claim 1, wherein, after the wireless communication has been established, the method further comprises:

comparing an idle time interval indicative of a time interval since the last data communication between the medical apparatus and the medical accessory using the wireless communication with a pre-defined maximum idle time interval; and closing the wireless communication in response to the idle time interval being greater than the pre-defined maximum idle time interval.

4. The method of claim 1, wherein, after the wireless operating communication has been established, the method further comprises:

providing a second medical apparatus comprising a readable element readable by at least one data acquisition unit and different than the readable element of the medical apparatus and the readable element of the medical component;

acquiring second configuration data associated to the readable element of the second medical apparatus by relatively approaching the data acquisition unit of the medical accessory and the readable element of the second medical apparatus;

closing the wireless communication between the medical accessory and the medical apparatus; and establishing a second wireless communication between the medical accessory and the second medical apparatus based on the second configuration data.

5. The method of claim 1, further comprising closing the wireless communication after the operation data has been provided.

6. The method of claim 1, wherein the medical accessory is a mobile communications device.

7. The method of claim 1, wherein acquiring configuration data associated to the readable element comprises:

detecting the presence of the readable element within a maximum operating distance to the data acquisition unit of the medical accessory.

8. The method of claim 1, wherein one or more of the readable element of the medical apparatus and the readable element of the medical component comprises an optical pattern, and wherein the data acquisition unit of the medical accessory comprises an optical reader to scan the optical pattern.

9. The method of claim 8, wherein providing the medical apparatus comprising a readable element comprises:

displaying the optical pattern on a display unit of the medical apparatus, and wherein acquiring configuration data associated to the readable element of the medical apparatus comprises:

optically scanning the optical pattern using the optical reader; and decoding the configuration data from the optical pattern.

10. The method of claim 9, wherein the display unit comprises a graphical input/output unit, the graphical input/output unit comprising a touch screen display.

11. The method of claim 1, further comprising operatively coupling the medical component to the medical apparatus.

12. The method of claim 1, further comprises closing the wireless communication after the operation data has been provided, the wireless communication being closed upon action of the medical apparatus after verifying completion of apparatus dressing with medical components.

13. The method of claim 1, wherein one or more of the readable element of the medical apparatus and the readable element of the medical component comprises a near field communication unit, the near field communication unit comprising a near field communication transmitter and receiver, and wherein the data acquisition unit of the medical accessory comprises a near field communication reader to read data from the near field communication transmitter and receiver and wherein acquiring configuration data associated to the readable element of the medical apparatus comprises:

sending an electromagnetic signal from the data acquisition unit of the medical accessory to the readable element of the medical apparatus, the electromagnetic signal being sent in order to supply energy to a transponder or transceiver comprised in the readable element;

receiving the configuration data in response to the electromagnetic signal and through an electromagnetic response signal; and decoding the configuration data from the electromagnetic response signal.

14. The method of claim 1, wherein the configuration data comprise one or more of:

identification data comprising a unique identifier of the medical apparatus on the medical apparatus, and wherein establishing the wireless communication between the medical accessory and the medical apparatus is based on the unique identifier;

type data indicative of one or more properties of the medical apparatus, and wherein establishing the wireless communication between the medical accessory and the medical apparatus comprises determining whether the medical apparatus is of a type configured for operation with the medical accessory based on one or more of the hardware data, the software data, and the firmware data; and status data indicative of an operating configuration of the medical apparatus, and wherein establishing the wireless communication between the medical accessory and the medical apparatus comprises determining, based on the status data, whether the medical apparatus is in a status configured for operation with the medical component.

15. The method of claim 14, wherein the one or more properties of the medical accessory that the type data are indicative of, comprise one or more properties of:

hardware data indicative of a hardware configuration of the medical accessory;

software data indicative of a software configuration of the medical accessory; and firmware data indicative of a firmware configuration of the medical accessory.

16. The method of claim 1, wherein acquiring the configuration data further comprises determining a validity of the configuration data and, in response to the medical accessory determining the configuration data to be invalid, preventing the wireless communication from being established, wherein determining the validity of the configuration data comprises determining the configuration data to be invalid in response to at least one of:

no configuration data have been acquired;

the configuration data acquired are incomplete; and a generated checksum computed based on the configuration data differs from a received checksum being received as a portion of the configuration data.

17. The method of claim 1, further comprising:
determining a validity of the operation data; and
signalling, in response to not being able to determine the validity of the operation data, wherein determining the validity of the operation data comprises determining the operation data to be invalid in response to at least one of:
no operation data have been acquired;
the operation data acquired are incomplete;
a generated checksum computed based on the operation data differs from a received checksum being received as a portion of the operation data;
an operating medical component is already operatively coupled to the medical apparatus and the operating medical component and the medical component are of a same type; and
the medical component is not configured to be operatively coupled to the medical apparatus.

18. The method of claim 1, wherein the medical apparatus is a blood treatment device configured for receiving a disposable blood circuit, the disposable blood circuit including a venous line, an arterial line, and a blood treatment unit, the medical apparatus comprises:
a support structure to receive a plurality of replaceable components of different categories in correspondence of respective operating areas of said medical apparatus, wherein said plurality of replaceable components comprise a plurality of components of different categories, each component of a same category having a respective mechanical connection to a corresponding operating area on the medical apparatus, different from that of components of other categories, and wherein said medical apparatus includes a plurality of different types of engaging means, each type of engaging means being designed for mechanically engaging, in a respective operating area, a component of one corresponding category only.

19. The method of claim 1, further comprising:
providing a new medical component comprising a readable element;
acquiring new operation data associated to the readable element of the new medical component by relatively approaching the medical accessory and the readable element of the new medical component;
providing the new operation data to the medical apparatus using the wireless communication; and
operatively coupling the new medical component to the medical apparatus, the above processes being repeatable for each new medical component of a plurality of new medical components.

20. A method for setting up a fluid processing medical apparatus, the method comprising:
providing the medical apparatus comprising a readable element readable by at least one data acquisition unit;
acquiring configuration data associated to the readable element of the medical apparatus by relatively approaching a data acquisition unit of a medical accessory and the readable element of the medical apparatus;
establishing a wireless communication between the medical accessory and the medical apparatus based on the configuration data;
providing a first medical component comprising a readable element different than the readable element of the medical apparatus;
acquiring first operation data associated to the readable element of the first medical component by relatively approaching the data acquisition unit of the medical accessory and the readable element of the first medical component;
providing the first operation data to the medical apparatus using the wireless communication and operatively coupling the first medical component to the medical apparatus;
providing a second medical component comprising a readable element readable by at least one data acquisition unit and different than the readable element of the medical apparatus and the readable element of the first medical component;
acquiring second operation data associated to the readable element of the second medical component by relatively approaching the data acquisition unit of the medical accessory and the readable element of the second medical component; and
providing the second operation data to the medical apparatus using the wireless communication and operatively coupling the second medical component to the medical apparatus, wherein the first medical component and the second medical component are of different medical component categories.

21. A method for providing operation data to a fluid processing medical apparatus, the method comprising:
providing the medical apparatus comprising a readable element readable by at least one data acquisition unit;
acquiring configuration data associated to the readable element of the medical apparatus by relatively approaching a data acquisition unit of a medical accessory and the readable element of the medical apparatus;
establishing a wireless communication between the medical accessory and the medical apparatus based on the configuration data;
providing a medical component comprising a readable element different than the readable element of the medical apparatus;
acquiring operation data associated to the readable element of the medical component by relatively approaching the data acquisition unit of the medical accessory and the readable element of the medical component, wherein the medical component is configured to be operatively coupled to the medical apparatus; and
providing the operation data to the medical apparatus using the wireless communication, wherein the configuration data comprises status data indicative of an operating configuration of the medical apparatus, and wherein establishing the wireless communication between the medical accessory and the medical apparatus comprises determining, based on the status data, whether the medical apparatus is in a status configured for operation with the medical component.

22. A method for providing operation data to a fluid processing medical apparatus among a plurality of medical apparatuses, the method comprising:
providing the medical apparatus comprising a readable element readable by at least one data acquisition unit;
acquiring configuration data associated to the readable element of said medical apparatus by relatively approaching a data acquisition unit of a medical accessory and the readable element of the medical apparatus, the configuration data comprising identification data comprising a unique identifier associated to said medical apparatus between the plurality of medical apparatuses;

establishing a wireless communication only between the medical accessory and said medical apparatus, between the plurality of medical apparatuses, based on the configuration data, the step of establishing the wireless communication between the medical accessory and the medical apparatus being further based on the unique identifier;

providing a medical component comprising a readable element different than the readable element of the medical apparatus;

acquiring operation data associated to the readable element of the medical component by relatively approaching the data acquisition unit of the medical accessory and the readable element of the medical component, wherein the medical component is configured to be operatively coupled to said medical apparatus; and providing the operation data to said medical apparatus between the plurality of medical apparatuses using the wireless communication.

23. The method of claim 1, wherein the operation data include at least one or more data selected in the group comprising identity of the medical component, identity of a series of identical medical components, expiration date of the medical component, manufacturer of the medical component, one or more commands for programming the medical apparatus to execute a procedure on the fluid, data concerning a patient.

* * * * *